United States Patent [19]

Iizuka et al.

[11] Patent Number: 4,841,067

[45] Date of Patent: Jun. 20, 1989

[54] NOVEL AMINO ACID DERIVATIVES

[75] Inventors: Kinji Iizuka; Tetsuhide Kamijo; Tetsuhiro Kubota, all of Nagano; Kenji Akahane, Tokyo; Hideaki Umeyama, Chiba; Yoshiaki Kiso, Osaka, all of Japan

[73] Assignee: Kissei Pharmaceutical Co., Ltd., Nagano, Japan

[21] Appl. No.: 233,962

[22] Filed: Aug. 19, 1988

Related U.S. Application Data

[63] Continuation of Ser. No. 824,341, Jan. 31, 1986, abandoned.

[30] Foreign Application Priority Data

| Jan. 31, 1985 | [JP] | Japan | 60-17563 |
| Feb. 14, 1985 | [JP] | Japan | 60-27972 |
| Mar. 1, 1985 | [JP] | Japan | 60-41614 |

[51] Int. Cl.$^4$ .................................. C07D 233/64
[52] U.S. Cl. .................................. 548/344
[58] Field of Search .......................... 548/344

[56] References Cited

U.S. PATENT DOCUMENTS

| 4,234,571 | 11/1980 | Nestor et al. | 548/344 |
| 4,548,926 | 10/1985 | Matsueda et al. | 548/344 |
| 4,591,648 | 5/1986 | Jones et al. | 548/344 |
| 4,656,269 | 4/1987 | Iizuka et al. | 548/344 |
| 4,666,888 | 5/1987 | Raddatz et al. | 548/344 |
| 4,698,329 | 10/1987 | Matsueda et al. | 548/344 |
| 4,711,958 | 12/1987 | Iizuka et al. | 548/344 |

FOREIGN PATENT DOCUMENTS

| 9227851 | 6/1983 | China | 548/344 |
| 0163899 | 2/1984 | China | 548/344 |
| 1275256 | 11/1984 | China | 548/344 |
| 173481 | 3/1986 | European Pat. Off. | 548/344 |
| 87/1004248 | 7/1988 | European Pat. Off. | 548/344 |
| 19100 | 8/1985 | Japan | 548/344 |
| 201036 | 4/1986 | Japan | 548/344 |
| 265921 | 12/1986 | Japan | 548/344 |
| 285317 | 12/1986 | Japan | 548/344 |

OTHER PUBLICATIONS

Colombo et al., Chem. Abstracts, vol. 101, 23914u (1984).
Brown et al., Chem. Abstracts, vol. 95, 220299f (1981).
Matsueda et al, "Short Chain Peptide Inhibitors of Human Renin", Chemistry Letters, Chem. Soc. Japan, No. 7, pp. 1041-1044 (1985).
Patent Abstracts of Japan, unexamined applications, C Section, vol. 2, No. 43, Mar. 23, 1978, p. 4928.

*Primary Examiner*—Mary C. Lee
*Assistant Examiner*—J. Richter
*Attorney, Agent, or Firm*—Sughrue, Mion, Zinn, Macpeak & Seas

[57] ABSTRACT

Novel amino acid derivatives useful as a therapeutic agent are disclosed. These amino acid derivatives and the pharmaceutically acceptable salts thereof have a human renin inhibitory effect when administered orally and are useful for treatment of hypertension, especially renin-associated hypertension.

21 Claims, No Drawings

NOVEL AMINO ACID DERIVATIVES

This is a continuation of application Ser. No. 824,341 filed 1/31/86, now abandoned.

FIELD OF THE INVENTION

This invention relates to novel amino acid derivatives useful as a therapeutic agent. More particularly, this invention relates to amino acid derivatives which have a human renin inhibitory effect when administered orally, and thus which are useful for treatment of hypertension, especially renin-associated hypertension.

BACKGROUND OF THE INVENTION

Renin is a proteolytic enzyme having a molecular weight of about 40,000, produced and secreted by juxtaglomerular cells in the kidney. This acts on the plasma renin substrate, angiotensinogen, to yield decapeptide angiotensin I which is converted into angiotensin II by an angiotensin I converting enzyme.

It is well known that angiotensin II contracts the vascular smooth muscle and acts on the adrenal cortex to secrete the aldosterone which regulates salts and water balance. Accordingly, the reninangiotensin system plays an important role in hypertension. In fact, a specific inhibitor of angiotensin I converting enyzme has been investigated and developed as a practical medicament for hypertension. Thus, an effective inhibitor of renin has long been sought as an agent for treatment of hypertension, especially renin-associated hypertension. As a result, it has been found that certain peptides show renin inhibitory effect, as described in Japanese Patent Application (OPI) Nos. 155345/84, 227851/84 and 110661/84, (The term "PIO" as used herein refers to an unexamined Japanese patent application); Japanese Patent Publication No. 39149/83, Biochemical and Biophysical Research Communications, Vol. 118, pages 929–933, 1984; and European Patent Application Nos. 77029($A_2$), 77028($A_2$) and 81783($A_2$).

Of these prior art references, Japanese Patent Application (OPI) No. 155345/84 discloses peptides represented by the following formula:

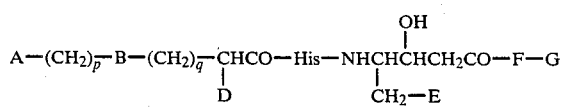

wherein A represents a hydrogen atom, a phenyl group or 10,11-dihydro-5H-dibenzo[a,d]cycloheptenyl group, B represents —O—, —CH═CH—, or —CH$_2$—, p and q, which may be the same or different, each represents an integer of from 0 to 3, D represents a hydrogen atom, a lower alkyl group, a lower alkenyl group, a phenyl group or a phenylalkyl group, E represents a phenyl group, a cyclohexyl group or an isopropyl group, His represents an L-histidyl group, F represents a residual group of an amino acid such as an L-leucyl, an L-isoleucyl, an L-leucyl-L-phenylalanyl, an L-phenylalanyl-L-phenyl-alanyl and an L-alanyl-L-phenylalanyl group, and G represents a protective group attached to the terminal carbon atom of an amino acid, such as an amino group, an arylalkylamino group and an alkoxy group.

Japanese Patent Application (OPI) No. 227851/84 also discloses peptides represented by the following formula:

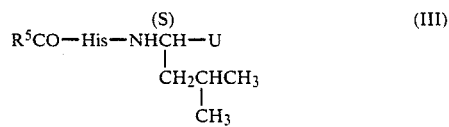

wherein R$^5$CO— represents an aliphatic acyl group, an aromatic acyl group, an aromatic aliphatic acyl group, a heterocyclic acyl group or a heterocyclic aliphatic acyl group, said acyl groups may be substituted with an amino, a protected amino, a hydroxy, a substituted dithio, an alkyl, an alkoxy, an alkoxycarbonyl, or a nitro group or a halogen atom, U represents a formyl group, or

wherein R$^6$ represents a hydrogen atom, an alkyl group, an alkyl group having a hydroxy, a mercapto, an amino, a carbamoyl, a formyl, an aromatic ring or a heterocyclic ring substituent, Z represents a hydroxy, a mercapto or a formyl group, or U represents

wherein R$^7$ represents a hydroxy group or an alkyl group having a hydroxy, a mercapto, an amino, a carbamoyl, or a formyl group, or an aromatic ring or a heterocyclic ring substituent, His represents an L-histidyl group, C$^{(S)}$ represents a carbon atom in the S-configuration, provided that, when U represents a formyl group, R$^5$CO— does not represent a benzyloxy-carbonyl-L-phenylalanyl group or a benzyloxycarbonyl-L-prolyl-L-phenylalanyl group.

The noted Biochemical and Biophysical Research Communications article discloses a peptide represented by the formula:

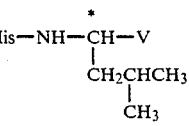

wherein W represents a benzyloxycarbonyl group, an N-benzyloxycarbonyl-L-phenylalanyl group or an N-benzyl-oxycarbonyl-3-(1-naphthyl)-L-alanyl group, V represents a formyl group or a hydroxy group and C* represents a carbon atom in the L-configuration.

Japanese Patent Publication No. 39149/83 discloses peptides represented by the following formula:

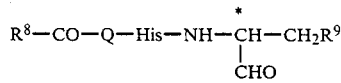

wherein R$^8$ represents a methyl group, an ethyl group, a benzyl group, an adamantyl group or a benzyloxy group, Q represents an L-phenylalanyl group, an L-pro-lyl-L-phenylalanyl group or an L-histidyl-L-proplyl-L-phenylalanyl group, His represents an L-histidyl group, $R^9$ represents an isopropyl group, and C* represents a carbon atom in the L-configuration. These peptides show a renin inhibitory effect. However, they are easily hydrolyzed by proteolytic enzymes of the gastrointestinal tract such as chymotrypsins. Therefore, these peptides have a drawback that their renin inhibitory effect can not be expected when they are administered orally.

On the other hand, the peptides disclosed in the above European Patent Applications are polypeptides and have difficulties in their preparation and purification. Furthermore, they lose their pharmacological effects when administered orally similar to the peptides disclosed in the Japanese Patent Publication No. 39149/83, and their utility is thus limited.

Thus, development of renin inhibitors which can display a sufficient therapeutic effect by oral administration has long been desired.

SUMMARY OF THE INVENTION

Accordingly, an object of this invention is to provide new amino acid derivatives which exhibit a specific renin inhibitory effect when administered orally to mammalia including humans.

Another object of this invention is to provide new amino acid derivatives and pharmaceutically acceptable salts thereof.

A further object of this invention is to provide pharmaceutical compositions comprising dipeptides or pharmaceutically acceptable salts thereof.

A still further object of this invention is to provide methods for the treatment of hypertension using new amino acid derivatives or pharmaceutically acceptable salts thereof.

Other objects, features and advantages of this invention will be apparent from the following description of the invention.

The present invention provides new amino acid derivatives represented by formula (I):

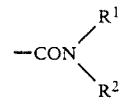

wherein $R^1$ represents a hydrogen atom, an alkyl group having 1 to 6 carbon atoms or an arakyl group having 7 to 10 carbon atoms and $R^2$ represents an alkyl group having 1 to 6 carbon atoms, or X represents —CH$_2$—Y—R wherein Y represents —O— or —NH— and R represents a straight or branched chain alkyl group having 1 to 6 carbon atoms or an aralkyl group having 7 to 10 carbon atoms, $C^{(+)}$ represents (+) form, His represents an L-histidyl group, C* represents a carbon atom in the L-configuration, m represents an integer of from 1 to 3, n represents 0 or 1; or pharmaceutically acceptable salts thereof.

DETAILED DESCRIPTION OF THE INVENTION

These amino acid derivatives of formula (I) of the present invention and pharmaceutically acceptable salts thereof inhibit renin activity in a human renin-sheep renin substrate system. Furthermore, the amino acid derivatives of the present invention are stable against proteolytic enzymes such as pepsin and chymotrypsins.

These findings demonstrate that the amino acid derivatives of formula (I) of the present invention exhibit a human renin inhibitory effect when administered orally to mammalia, including humans, and thus are useful for treatment of hypertension, especially renin-associated hypertension.

The amino acid derivatives of formula (I) of the present invention can be prepared according to a well known method. That is, of the amino acid derivatives of formula (I) of the present invention, the amino acid derivatives of formula:

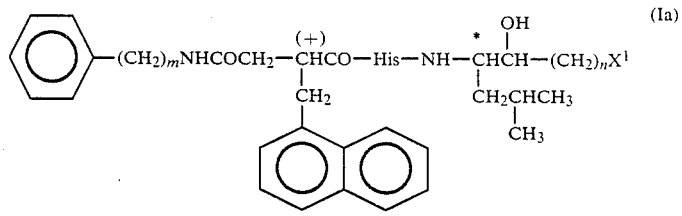

wherein $X^1$ represents a straight or branched chain alkoxycarbonyl group having 2 to 10 carbon atoms, an aralkoxycarbonyl group having 8 to 10 carbon atoms,

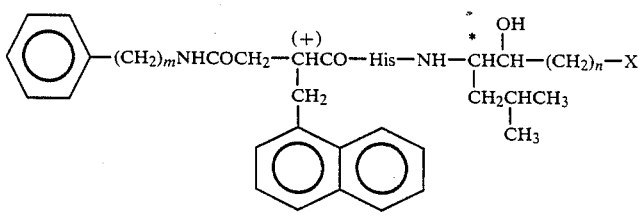

wherein X represents a straight or branched chain alkoxycarbonyl group having 2 to 10 carbon atoms, an aralkoxycarbonyl group having 7 to 10 carbon atoms, a hydroxymethylgroup, or

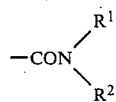

wherein $R^1$ represents a hydrogen atom, an alkyl group having 1 to 6 carbon atoms or an aralkyl group having 7 to 10 carbon atoms and $R^2$ represents an alkyl group having 1 to 6 carbon atoms or $-CH_2-Y-R$ wherein Y represents $-O-$ or $-NH-$ and R represents a straight or branched chain alkyl group having 1 to 6 carbon atoms or an aralkyl group having 7 to 10 carbon atoms, m, $C^{(+)}$, His, $C^*$ and n have the same meanings as defined above, can be prepared by reacting a compound of formula:

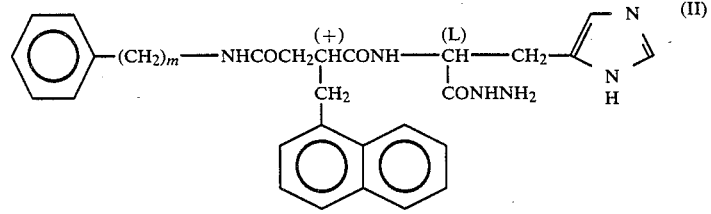

wherein $C^{(L)}$ means a carbon atom in the L-configuration, and $C^{(+)}$ has the same meaning as defined above, with a compound of formula:

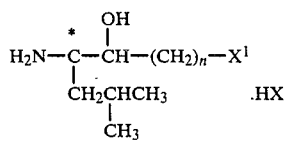

wherein $C^*$, n and $X^1$ have the same meanings as defined above, and HX represents hydrochloric acid, trifuoroacetic acid or p-toluenesulfonic acid.

One of the amino acid derivatives of the present invention, the amino acid derivatives of formula:

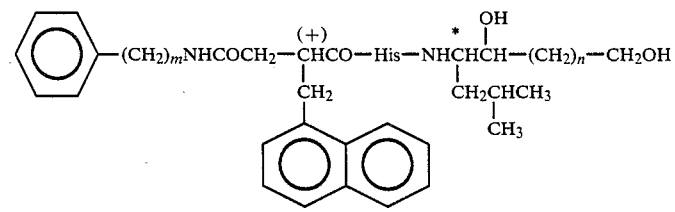

wherein m, $C^{(+)}$, $C^*$ have the same meanings as defined above, can be prepared by reducing the amino acid derivatives of formula (Ia) wherein $X^1$ is a methoxycarbonyl group, with sodium borohydride.

The compounds of formula (II) used as a starting material can be prepared by reacting a reactive functional derivative of an acid compound of formula:

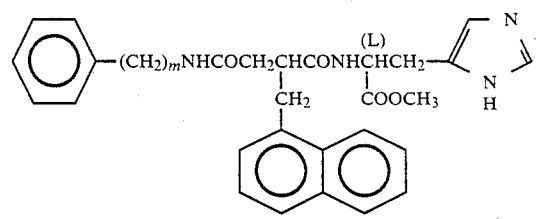

wherein m has the same meaning as defined above, with L-histidine methyl ester dihydrochloride in N,N-dimethylformamide to obtain a compound of formula:

(V)

wherein m and $C^{(L)}$ have the same meanings as defined above, reacting the resulting compound with hydrazine monohydrate in methanol, and then recrystallizing the obtained diastereoisomeric mixture or separating and purifying the same mixture by using column chromatography. Alternatively, the compounds of formula (II) can also be prepared by reacting a reactive functional derivative of an acid compound of formula:

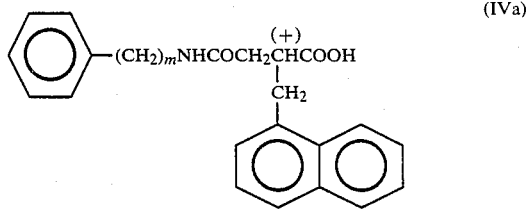

wherein $C^{(+)}$ and m have the same meanings as defined above, with L-histidine methyl ester dihydrochloride in N,N-dimethylformamide to obtain a compound of formula:

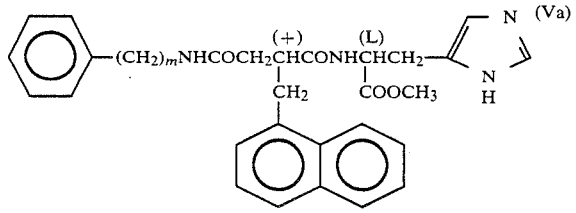

wherein $C^{(+)}$, $C^{(L)}$ and m have the same meanings as defined above, and then reacting the resulting compound with hydrazine monohydrate in methanol.

The acid compounds of formula (IV) above can be prepared by the method described below or an analogous method thereof. That is, the acid compounds of formula (IV) can be prepared by reacting 1-naphthaldehyde with diethyl succinate to obtain the compound of the formula:

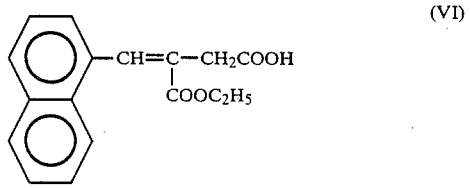

hydrolyzing the resulting compound to obtain the corresponding dicarboxylic acid, dehydrating the dicarboxylic acid compound obtained in acetic anhydride, reacting the resulting compound with a phenylalkylamine to obtain a compound of formula:

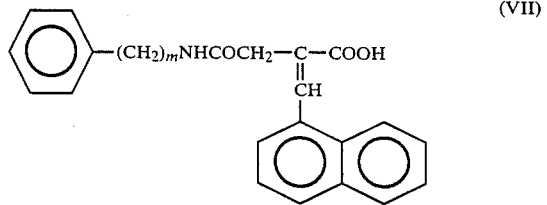

wherein m has the same meaning as defined above, and then hydrogenating the resulting compound over palladium charcoal.

The acid compounds of formula (IVa) above can be prepared from the acid compound of formula (IV) according to a conventional optical resolution method.

That is, the (+) form compound of the acid compound of formula (IVa) can be prepared by using (+)-α-methyldibenzylamine as an optically active amine.

The (−) form compound of the acid compound of formula (IV) can also prepared by using (−)-α-methyldibenzylamine.

The compounds of formula (III) used as starting material can be prepared by methods described in literature or an analogous method thereof. That is, the compound wherein n is 0 can be prepared from 3-amino-3-hydroxy-5-methylhexanoic acid which is prepared according to the method described in J. Org. Chem., Vol. 45, pages 2288–2290, 1980. The compound wherein n is 1 can be prepared from statine or N-(tert-butyloxycarbonyl)statine.

The reaction of a compound of formula (II) with a compound of formula (III) can be carried out according to the following manner.

That is, the amino acid derivative of formula (I) of the present invention can be prepared by suspending a compound of formula (II) in N,N-dimethylformamide, adding hydrogen chloride in a proportion of from about 3 to about 5 molar amounts per mole of the compound of formula (II) to the suspension, adding isoamyl nitrite in a proportion of from about 1 to about 3 molar amounts per mole of the compound of formula (II) to the mixture, reacting the mixture for about 5 to about 30 minutes at about −20° to about −5° C., adjusting a pH of the reaction mixture to about 8 to about 9 by adding triethylamine, adding dropwise the mixture to a solution of the compound of formula (III) and triethylamine in an equimolar amount to the compound of formula (II) in N,N-dimethylformamide under icecooling, preferably −20° to 0° C., reacting the mixture for about 5 to about 20 hours at 0° C. or at room temperature, adding a 5% aqueous sodium bicarbonate solution and extracting with ethyl acetate, evaporating the ethyl acetate layer, and then purifying the residue by preparative silica gel thin layer chromatography.

The amino acid derivatives of formula (I) of the present invention can be converted according to conventional methods to a pharmaceutically acceptable salt thereof. Examples of such pharmaceutically acceptable salts include pharmaceutically acceptable inorganic or organic acid salts such as a hydrochloric acid salt, a sulfuric acid salt, a p-toluenesulfonic acid salt, an acetic acid salt, a citric acid salt, a tartaric acid salt, a succinic acid salt, a fumaric acid salt and the like. These salts have a renin inhibitory effect as high as the corresponding compound having a free amino group and are stable against proteolytic enzymes, and thus they show the desired renin inhibitory effect even by oral administration.

The amino acid derivatives of formula (I) of the present invention possess a strong inhibitory effect on human renin and are useful as a therapeutically active agent for treatment of hypertension, especially renin-associated hypertension.

The amino acid derivatives of formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The amino acid derivatives and the pharmaceutically acceptable salts of the general formula (I) of the present invention can be administered in various dosage forms depending upon the intended therapy. Typical dosage forms which can be used are tablets, pills, powders, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipient such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated into sugarcoated tablets, gelatin-coated tablets, film-coated tablets, or tablets coated with two or more layers.

When the pharmaceutical composition is formulated into an injectable preparation, it is preferred that the resulting injectable solution and suspension are sterilized and rendered isotonic with respect to blood. In making the pharmaceutical composition in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the amino acid derivatives of the present invention may be in the range of from about 5 mg to 5,000 mg per adult human by oral administration per day, or from about 1 mg to 1,000 mg per adult human by parenteral administration per day in multiple doses depending upon the type of disease, the severity of condition to be treated, and the like.

This invention is further illustrated in more detail by way of the following examples and reference examples. The melting point of the product obtained was uncorrected. The NMR spectra of the products were measured by JEOL's High Resolution NMR Spectrometer Type JNM-GX 270. The Mass spectra of the products were measures by JEOL's Mass Spectrometer Type JMN-DX 300 according to the FAB method. Thin layer chromatography was carried out using Merck's precoated plates silica gel 60 $F_{254}$ and column chromatography was carried out by employing Merck's Kiesel gel 60 (230–400 mesh). Thin layer chromatography was carried out by using a lower layer of a mixture of chloroform, methanol and water in a proportion of 8/3/1 (by volume) (mixture A) and a mixture of chloroform and methanol in a proportion of 5/1 (by volume) (mixture B) as a developing solvent, and an $Rf_1$ (mixture A) value and $Rf_2$ (mixture B) value were calculated.

REFERENCE EXAMPLE 1

(±)-2-(1-Naphthylmethyl)-3(phenethylcarbamoyl)-propionic acid

To a solution of 17.40 g of ethyl succinate and 15.62 g of 1-naphthaldehyde in 100 ml of absolute ethanol was added 6.00 g of sodium hydride (50% dispersion in mineral oil), and the mixture was heated under reflux for 3 hours. The reaction mixture was evaporated under reduced pressure, and water was added to the residue. The mixture was extracted with diethyl ether to remove neutral materials. The aqueous layer was acidified by adding concentrated hydrochloric acid, and extracted with diethyl ether. The ethereal layer was washed with a saturated sodium chloride aqueous solution, dried over anhydrous magnesium sulfate, and evaporated under reduced pressure to obtain 23.60 g of 3-ethoxycarbonyl-4-(1-naphthyl)-3-butenoic acid as a yellow oil. A mixture of 200 ml of a 1N-aqueous sodium hydroxide solution and 170 ml of ethanol was added to 23.50 g of the butenoic acid obtained. The mixture was heated at 50° C. for 1.5 hours. The reaction mixture was evaporated under reduced pressure, and water was added to the residue. The mixture was extracted with diethyl ether to remove neutral materials. The ethereal layer was washed with a saturated sodium chloride aqueous solution, dried over anhydrous magnesium sulfate, and evaporated under reduced pressure to obtain 15.30 g of 2-(1-naphthylmethylene)succinic acid as yellow crystals.

To 260 ml of acetic anhydride was added 15.20 g of 2-(1-naphthylmethylene)succinic acid, and the mixture was heated under reflux for 1 hour. The reaction mixture was evaporated under reduced pressure, and 100 ml of dry benzene was added to the residue. The precipitated crystals were collected by filtration to obtain 6.80 g of 2-(1-naphthylmethylene)succinic anhydride as orange yellow crystals.

In 60 ml of dichloromethane were dissolved 3.00 g of the succinic anhydride and 1.52 g of phenethylamine, and the mixture was stirred for 2 hours at room temperature. The precipitated crystals were collected by filtration to obtain 4.02 g of 2-(1-naphthylmethylene)-3-(phenethylcarbamoyl)propionic acid as colorless crystals.

Melting point: 183°–187° C. IR (KBr): $\nu co$ 1670, 1640 $cm^{-1}$. NMR ($d_6$-DMSO); δ: 2.69(t, 2H, J=7.1 Hz), 3.15(s, 2H), 3.26(t, 2H, J=7.1 Hz), 7.1–8.1(m, 13H), 8.20(s, 1H).

A solution of 4.00 g of 2-(1-naphthylmethylene)-3-(phenethylcarbamoyl)propionic acid in 120 ml of acetic acid was hydrogenated over 2.0 g of a 10% palladium-charcoal under a hydrogen atmosphere at room temperature. After filtration of the catalyst, the filtrate was evaporated under reduced pressure, and hexane was added to the residue. The precipitated crystals were collected by filtration to obtain 3.40 g of (±)-2-(1-naphthylmethyl)-3-(phenethylcarbamoyl)-propionic acid as colorless crystals.

Melting point: 131°–135° C. IR (KBr): $\nu co$ 1720, 1640 $cm^{-1}$. NMR ($d_6$-DMSO); δ: 2.15–2.55(m, 2H), 2.68(t, 2H, J=7.1 Hz), 3.0–3.5(m, 5H), 7.1–8.2(m, 13H).

REFERENCE EXAMPLE 2

The optical resolution of (±)-2-(1-naphthylmethyl)-3-phenethylcarbamoyl)propionic acid To a solution of 1.0 g of (±)-2-(1-naphthylmethyl)-3-(phenethylcarbamoyl)propionic acid in 20 ml of methanol was added a solution of 335 mg of (+)-α-methylbenzylamine in 10 ml of methanol, and the mixture was evaporated under reduced pressure. The residue was recrystallized three times from ethyl acetate to obtain 330 mg of white crystals. Water, a 1N-hydrochloric acid and ethyl acetate were added to the white crystals obtained, and the ethyl acetate layer was separated. The ethyl acetate layer was washed with a 0.1N-hydrochloric acid, dried over anhydrous magnesium sulfate, and evaporated under reduced pressure. The residue was purified by silica gel column chromatography (eluent: chloroform/ethanol=10/1 by volume) to obtain 220 mg of (+)-(2-(1-naphthylmethyl)-3-(phenethylcarbamoyl)propionic acid as a white powder.

Melting point: 146°–150° C. Ir (KBr): $\nu co$ 1705, 1635 $cm^{-1}$. NMR (CDCl$_3$); δ: 2.25–2.55(m, 2H), 2.74(t, 2H, J=7.1 Hz), 3.12(dd, 1H, J=9.9, 13.7 Hz), 3.2–3.6(m, 3H), 3.73(dd, 1H, J=5.0, 13.7 Hz), 5.45–5.6(m, 1H), 7.0–8.15(m, 12H).

$[\alpha]_D^{21}$ +7.3° (methanol, C=1.00)

REFERENCE EXAMPLE 3

In a manner similar to Reference Example 2, except that (−)-α-methylbenzylamine was used in place of the (+)-α-methylbenzylamine used in Reference Example 2, (−)-2-(1-naphthylmethyl)-3-(phenethylcarbamoyl)-propionic acid was obtained.

Melting point: 147°–151° C. IR (KBr): νco 1705, 1635 cm$^{-1}$. NMR (CDCl$_3$); δ: 2.3–2.5(m, 2H), 2.75(t, 2H, J=7.1 Hz), 3.11(dd, 1H, J=10.5, 13.8 Hz), 3.2–3.6 (m, 3H), 3.75(dd, 1H, J=5.0, 14.3 Hz), 5.4–5.6(m, 1H), 7.05–8.15(m, 12H).

$[α]_D^{23}$ −6.2° (methanol C=1.00).

REFERENCE EXAMPLE 4

N-[2-(1-Naphthylmethyl)-3-(phenethylcarbamoyl)-propionyl]-L-histidine hydrazide To a suspension of 3.00 g of (±)-2-(1-naphthylmethyl)-3-(phenethylcarbamoyl)propionic acid and 2.01 g of L-histidine methyl ester dihydrochloride in 24 ml of N,N-dimethylformamide were added successively 2.16 ml of diphenylphosphoryl azide and 3.81 ml of triethylamine under ice-cooling, and the mixture was stirred for 16 hours under ice-cooling. The reaction mixture was evaporated under reduced pressure, and a 5% aqueous sodium bicarbonate solution was added to the residue. The mixture was extracted with ethyl acetate. The ethyl acetate layer was washed with water, dried over anhydrous magnesium sulfate, and evaporated under reduced pressure. Diethyl ether was added to the residue, the precipitated crystals were collected by filtration to obtain 4.08 g of N-[(±)-2-(1-naphthylmethyl)-3-(phenethylcarbamoyl)propionyl]-L-histidine methyl ester as a white powder. To a solution of 4.00 g of the ester compound obtained in 25 ml of methanol was added 2.75 g of hydrazine monohydrate, and the mixture was stirred for 4 hours at room temperature. The reaction mixture was evaporated under reduced pressure. The residue was washed with diethyl ether, and dried under reduced pressure below 40° C. to obtain 3.90 g of N-[(±)-2-(1-naphthylmethyl)-3-(phenethylcarbamoyl)propionyl]-L-histidine hydrazide as a white powder. In 5 ml of methanol was dissolved 2.20 g of the hydrazide compound obtained with heating at 40° C., and insoluble materials were filtered off. The filtrate was allowed to stand overnight at room temperature, and then precipitated crystals were collected by filtration to obtain 0.70 g of N-[(±)-2-(1-naphthylmethyl)-3-(phenethylcarbamoyl)propionyl]-L-histidine hydrazide as a white powder.

$[α]_D^{10}$ +20.6° (methanol C=0.19).

Melting point: 214°–218° C. Rf$_1$: 0.53. MS: MH+, 513.

Then, 200 ml of diethyl ether was added to the filtrate, and precipitated crystals were filtered off. The filtrate was evaporated under reduced pressure, and diethyl ether was added to the residue. The precipitated crystals were collected by filtration and recrystallized from a mixture of dichloromethane and methanol (10:1 by volume) to obtain 1.10 g of N-[(−)-2-(1-naphthylmethyl)-3-(phenethylcarbamoyl)propionyl]-L-histidine hydrazide as a white powder.

$[α]_D^{10}$ −47.0° (methanol C=0.20).

Melting point: 145°–148° C. Rf$_1$: 0.54. MS: MH+, 513.

The hydrazide compounds had the same IR, NMR, specific rotation and MS spectra as those of the hydrazide compounds derived from optically resolved (+) and (−)-2-(1-naphthylmethyl)-3-(phenethylcarbamoyl)-propionic acids.

REFERENCE EXAMPLE 5

(2RS, 3S)-3-Amino-2-hydroxy-5-methylhexanoic acid

A solution of 3.43 g of sodium hydrogen sulfite in 20 ml of water was added to 2.81 g of N-carbobenzoxy-L-leucinal, and the mixture was stirred for 14 hours under ice-cooling. A solution of 1.41 g of potassium cyanide in 50 ml of water and 200 ml of ethyl acetate were added successively to the reaction mixture. The ethyl acetate layer was washed with a saturated sodium chloride aqueous solution, dried over anhydrous magnesium sulfate, and evaporated under reduced pressure to obtain 2.54 g of 3-carbobenzoxyamino-2-hydroxy-5-methylhexanenitrile. To 500 mg of the nitrile were added 20 ml of dioxane and 20 ml of concentrated hydrochloric acid, and the mixture was heated under reflux for 12 hours. The reaction mixture was evaporated under reduced pressure, and the residual crystals were purified by cation exchange column chromatography (eluent: a 2N aqueous NH$_4$OH solution) to obtain 254 mg of (2RS, 3S)-3-amino-2-hydroxy-5-methylhexanoic acid as colorless crystals (a mixture ratio of 2R and 2S being about 7:3).

Melting point: 137°–140° C. IR (KBr): νco 1570 cm$^{-1}$. NMR (D$_2$O); δ: 0.8–1.0(m, 6H), 1.2–1.4(m, 2H), 1.55–1.8(m, 1H), 3.0–3.4(m, 1H), 3.89(d, 0.7H, J=3.3 Hz), 4.00(d, 0.3H, J=3.3 Hz). MS: MH+, 162.

REFERENCE EXAMPLE 6

(2RS, 3S)-3-tert-Butyloxycarbonylamino-2-hydroxy-5-methylhexanoic acid

To a solution of 3.22 g of (2RS, 3S)-3-amino-2-hydroxy-5-methylhexanoic acid and 3.08 ml of triethylamine in 30 ml of water was added a solution of 5.41 g of 2-(tert-butyloxycarbonyloxyimino)-2-phenylacetonitrile in 30 ml of dioxane, and the mixture was stirred for 16 hours at room temperature. To the reaction mixture was added 100 ml of water, and the mixture was extracted with ethyl acetate to remove neutral materials. The aqueous layer was acidified by adding citric acid, and the aqueous solution was extracted with ethyl acetate. The ethyl acetate layer was washed with a saturated sodium chloride aqueous solution, dried over anhydrous magnesium sulfate, and evaporated under reduced pressure to obtain 5.10 g of (2RS, 3S)-3-tert-butyloxycarbonylamino-2-hydroxy-5-methylhexanoic acid as a pale yellow oil.

IR (neat): νco 1710, 1675 cm$^{-1}$. NMR (CDCl$_3$); δ: 0.8–1.0(m, 6H), 1.2–1.85(m, 12H), 3.95–4.4(m, 2H), 4.8–5.0(br, 1H), 9.4–10.4(br, 1H).

REFERENCE EXAMPLE 7

(3S)-3-Carbobenzoxyamino-5-methyl-1,2-epoxyhexane

To a solution of 12 g of methyltriphenylphosphonium bromide in 100 ml of dry tetrahydrofuran was added 19.5 ml of n-butyl lithium (as a 1.6 mole hexane solution) under an argon atmosphere, and the mixture was stirred for 1 hour at room temperature. The reaction mixture was cooled below 5° C., and a solution of 7.5 g of N-carbobenzoxy-L-leucinal in 20 ml of dry tetrahydrofuran was added to the reaction mixture. The mixture was stirred for 1 hour at room temperature. An aqueous ammonium chloride solution was added to the reaction mixture, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: dichloromethane) to obtain 1.6 g of (3S)-3-carbobenzoxyamino-5-methyl-1-hexene as a colorless oil.

IR (neat): $\nu$co 1690 cm$^{-1}$. NMR (CDCl$_3$); δ: 0.85–0.95(m, 6H), 1.3–1.75(m, 3H), 4.15–4.25(m, 1H), 4.61(s, 1H), 5.05–5.2(m, 2H), 5.10(s, 2H), 5.74(ddd, 1H, J=6.0, 10.0, 17.0 Hz), 7.35(s, 5H).

To a solution of 600 mg of 3-chloroperoxybenzoic acid in 5 ml of dry chloroform was added a solution of 850 mg of (3S)-3-carbobenzoxyamino-5-methyl-1-hexene in 5 ml of dry chloroform under ice-cooling, and the mixture was stirred for 16 hours. Dichloromethane was added to the reaction mixture, and the mixture was successively washed with an aqueous sodium thiosulfate solution, a 5% aqueous sodium bicarbonate solution and a saturated sodium chloride aqueous solution, dried over anhydrous magnesium sulfate, and evaporated under reduced pressure. The residue was purified by silica gel flash column chromatography (eluent: benzene/hexane=1/1 by volume) to obtain 401 mg of (3S)-3-carbobenzoxyamino-5-methyl-1,2-epoxyhexane as a colorless oil.

IR (neat): $\nu$co 1695 cm$^{-1}$. NMR (CDCl$_3$); δ: 0.85–1.0(m, 6H), 1.35–1.8(m, 3H), 2.58(t, 1H, J=4.4 Hz), 2.72(t, 1H, J=4.4 Hz), 2.99(s, 1H), 3.95–4.1(m, 1H), 4.45–4.55(m, 1H), 5.09(s, 2H), 7.34(s, 5H).

EXAMPLE 1

Methyl (3S)-3-{N-[(+)-2-(1-naphthylmethyl)-3-(phenethylcarbamoyl)propionyl]-L-histidyl}amino-2-hydroxy-5-methylhexanoate (2RS, 2S and 2R forms)

Hydrogen chloride was passed into a solution of 110 mg of (2RS, 3S)-3-amino-2-hydroxy-5-methylhexanoic acid in 10 ml of methanol under ice-cooling, and the mixture was stirred overnight. The reaction mixture was evaporated under reduced pressure to obtained 150 mg of methyl (2RS, 3S)-3-amino-2-hydroxy-5-methylhexanoate hydrochloride as a white powder [IR (KBr): $\nu$co 1740 cm$^{-1}$].

To a solution of 154 mg of N-[(+)-2-(1-naphthylmethyl)-3-(phenethylcarbamoyl)propionyl]-L-histidine hydrazide in 4 ml of N,N-dimethylformamide were added successively dropwise 0.19 ml of a dry 5.1N-hydrogen chloride in N,N-dimethylformamide solution and 0.5 ml of isoamyl nitrite at −20° C., and the mixture was stirred. After disappearance of the hydrazide compound, the reaction mixture was cooled to −30° C., and neutralized by adding 0.14 ml of triethylamine to prepare a solution of [(+)-2-(1-naphthylmethyl)-3-(phenethylcarbamoyl)propionyl]-L-histidine azide. The azide solution obtained was added dropwise to a solution of methyl (2RS, 3S)-3-amino-2-hydroxy-5-methylhexanoate hydrochloride in 2 ml of N,N-dimethylformamide under ice-cooling, and the mixture was stirred for 16 hours. A 5% aqueous sodium bicarbonate solution was added to the reaction mixture, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol=10/1 by volume) to obtain 120 mg of methyl (2RS, 3S)-3-{N-[(+)-2-(1-naphthylmethyl)-3-(phenethylcarbamoyl)propionyl]-L-histidyl}amino-2-hydroxy-5-methylhexanoate as a white powder. The product was a mixture of 2S and 2R forms about in the ratio of 3:7.

Melting point: 82°–87° C. Rf$_1$: 0.58. MS: MH+, 656.

The ester compound obtained was carefully purified by silica gel flash column chromatography (eluent: chloroform/methanol=15/1 by volume) to obtain 28 mg of methyl (2S, 3S)-3-{N-(+)-2-(1-naphthylmethyl)-3-(phenethylcarbamoyl)propionyl]-L-histidyl}amino-2-hydroxy-5-methylhaxanoate and 66 mg of the corresponding 2R, 3S form compound as a white powder, respectively.

(2S, 3S) form compound

Melting point: 92°–95° C. Rf$_1$: 0.59. Rf$_2$: 0.54. MS: MH+, 656. (2R,3S) form compound Melting point: 91°–95° C. Rf$_1$: 0.58. Rf$_2$: 0.49. MS: MH+, 656.

The dipeptides obtained had the same IR, NMR and MS spectra as those of the products obtained from (2S,3S) and (2R,3S)-3-amino-2-hydroxy-5-methyl hexanes which are disclosed in J. Med. Chem. 25, 605–610, (1982). cl EXAMPLE 2

Isoamyl (2RS,3S)-3-{N-[(+)-2-(1-naphthylmethyl)-3-(phenethylcarbamoyl)propionyl]-L-histidyl}amino-2-hydroxy-5-methylhexanoate Hydrogen chloride was passed into a solution of 70 mg of (2RS,3S)-3-amino-2-hydroxy-5-methylhexanoic acid in 10 ml of isoamyl alcohol under ice-cooling, and the mixture was stirred overnight. The reaction mixture was evaporated under reduced pressure to obtain 110 mg of the ester hydrochloride as a colorless oil. [IR (neat): $\nu$co 1735 cm$^{-1}$].

To a suspension of 200 mg of N-[(+)-2-(1-naphthylmethyl)-3-(phenethylcarbamoyl)propionyl]-L-histidine hydrazide in 5 ml of N,N-dimethylformamide were added successively dropwise 0.25 ml of a dry 5.1N-hydrogen chloride in N,N-dimethyformamide solution and 0.07 ml of isoamyl nitrite with stirring at −20° C. After disappearance of hydrazide compound, the reaction mixture was cooled to −30° C., and neutralized by adding 0.2 ml of triethylamine to prepare a solution of N-[(+)-2-(1-naphthylmethyl)-3-(phenethylcarbamoyl)propionyl]-L-histidine azide. The azide solution prepared was added dropwise to 110 mg of isoamyl (2RS,3S)-3-amino-2-hydroxy-5-methylhexanoate and 0.1 ml of triethylamine in 2 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was dried over anhydrous magnesium sulfate and evaporated under reduced pressure. The pressure was purified by silica gel column chromatography (eluent: chloroform/ethanol=10/1 by volume) to obtain 52 mg of isoamyl (2RS,3S)-3-{N-[(+)-2-(1-naphthylmethyl)-3-(phenethylcarbamoyl)propionyl]-L-histidyl}amino-2-hydroxy-5-methylhexanoate as a white powder.

Melting point: 82°–87° C. Rf$_1$: 0.73. Rf$_2$: 0.69. MS: MH+, 712.

EXAMPLE 3

Benzyl (2RS,3S)-3-{N-[(+)-2-(1-naphthylmethyl)-3-(phenethylcarbamoyl)propionyl]-L-histidyl}amino-2-hydroxy-5-methylhexanoate In 5 ml of benzyl alcohol were dissolved 170 mg of (2RS,3S)-3-tert-butyloxycarbonylamino-2-hydroxy-5-methylhexane and 134 mg of p-toluenesulfonic acid (anhydrous) with heating at 110°–120° C., and 30 ml of dry benzene was added to the solution. The mixture was heated under reflux for 16 hours while removing water formed during the reaction using a molecular sieve. The reaction mixture was concentrated under reduced pressure, and diethyl ether was added to the residue. The precipitated crystals were collected by filtration to obtain 176 mg of p-toluenesulfonic acid salt of benzyl (2RS,3S)-3-amino-2-hydroxy-5-methyl-hexanoate as a white powder. [IR (KBr): $\nu$co 1725 cm$^{-1}$].

To a solution of 110 mg of N-[(+)-2-(1-naphthylmethyl)-3-(phenethylcarbamoyl)propionyl]-L-histidine hydrazide in 2 ml of N,N-dimethylformamide were added successively dropwise 0.15 ml of a dry 5.1N-hydrogen chloride in N,N-dimethylformamide and 0.038 ml of isoamyl nitrite at −20° C., and then the mixture was stirred. After disappearance of hydrazide compound, the reaction mixture was cooled to −30° C., and neutralized by adding 0.11 ml of triethylamine to prepare a solution of N-[(+)-2-(1-naphthylmethyl)-3-(phenethylcarbamoyl)propionyl]-L-histidine azide. The azide solution prepared was added to a solution of 100 mg of p-toluenesulfonic acid salt of benzyl (2RS,3S)-3-amino-2-hydroxy-5-methylhexanoate and 0.33 ml of triethylamine in 2 ml of N,N-dimethylformamide under ice-cooling, and the mixture was stirred for 16 hours under ice-cooling. A 5% aqueous sodium bicarbonate solution was added to the reaction mixture, and the mixture was extracted with ethyl acetate. The ethyl acetate layer was washed with a saturated sodium chloride aqueous solution, dried over magnesium sulfate, and evaporated under reduced pressure. The residue was purified by preparative silica gel thin layer chromotography (developing solvent: lower layer of chloroform/methanol/water=8/3/1 by volume) to obtain 65 mg of benzyl (2RS,3S)-3-{N-[(+)-2-(1-naphthylmethyl)-3-(phenethylcarbamoyl)propionyl]-L-histidyl-}amino-2-hydroxy-5-methylhexanoate as a white powder.

Melting point: 81°–86° C. Rf$_1$: 0.63. Rf$_2$: 0.62. MS: MH+, 732.

EXAMPLE 4

Methyl N-[(+)-2-(1-naphthylmethyl)-3-(phenethylcarbamoyl)-propionyl]-L-histidylstatinate Hydrogen chloride was passed into a solution of 100 mg of N-(tert-butyloxycarbonyl)statine (commercially available) in 20 ml of an absolute methanol under ice-cooling, and the mixture was stirred overnight at room under reduced pressure to obtain 81 mg of methyl statinate hydrochloride as a colorless oil. [IR (neat): $\nu$co 1725 cm$^{-1}$].

To a suspension of 90 mg of N-[(+)-2-(1-naphthylmethyl)-3-(phenethylcarbamoyl)propionyl]-L-histidine hydrazide in 5 ml of dry N,N-dimethylformamide were successively added 0.12 ml of a dry 5.1N-hydrogen chloride in N,N-dimethylformamide and 0.03 ml of isoamyl nitrite at −20° C. After disappearance of hydrazide compound, the reaction mixture was cooled to −30° C., and neutralized by adding 0.08 ml of triethylamine to prepare a solution of N-[(+)-2-(1-naphthylmethyl)-3-(phenethylcarbamoyl)propionyl]-L-histidine azide.

The azide solution prepared was added to a solution of 40 mg of methyl statinate hydrochloride and 0.03 ml of triethylamine in 2 ml of dry N,N-dimethylformamide under ice-cooling. The mixture was stirred for 16 hours under ice-cooling, and the reaction mixture was evaporated under reduced pressure. A 5% aqueous sodium bicarbonate solution was added to the residue, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol=15/1 by volume) to obtain 16 mg of methyl N-[(+)-2-(1-naphthylmethyl)-3-(phenethylcarbamoyl)propionl]-L-histidylstatinate as a white powder.

Melting point: 90°–94° C. Rf$_1$: 0.67. Rf$_2$: 0.65. MS: MH+, 670.

EXAMPLE 5

(3S)-3-{[(+)-2-(1-naphthylmethyl)-3-(phenethylcarbamoyl)propionyl]-L-histidyl}amino-2-hydroxy-5-methylhexanoylmethylamide (racemic mixture, isomers A and B)

To a solution of 261 mg of (2RS,3S)-3-tert-butyloxycarbonylamino-2-hydroxy-5-methylhexanoic acid, 0.12 ml of a 30% aqueous methylamine solution and 176 mg of 1-hydroxybenzotriazole in 2 ml of N,N-dimethylformamide and 2 ml of tetrahydrofuran was added 206 mg of dicyclohexylcarbodiimide with stirring under cooling, and the mixture was stirred for 16 hours under ice-cooling. The reaction mixture was cooled on an ice-bath, and insoluble materials were filtered off. The filtrate was evaporated under reduced pressure. The residue was dissolved in ethyl acetate, and the ethyl acetate was washed successively with an aqueous citric acid solution, a 5% aqueous sodium bicarbonate solution and a saturated sodium chloride aqueous solution, dried over anhydrous magnesium sulfate, and evaporated under reduced pressure to obtain 267 mg of (2RS,3S)-3-tert-butyloxycarbonylamino-2-hydroxy-5-methylhexanoylmethylamide as a white powder. [IR (KBr): $\nu$co 1690, 1625 cm$^{-1}$].

To a solution of 260 mg of the amide compound obtained in 5 ml of methanol was added 2 ml of a 2N-hydrochloric acid, and the mixture was stirred for 16 hours at room temperature. The reaction mixture was evaporated under reduced pressure to obtain 189 mg of (2RS,3S)-3-amino-2-hydroxy-5-methylhexanoylmethylamide hydrochloride as a white powder. [IR (KBr): $\nu$co 1650 cm$^{-1}$].

To a solution of 102 mg of N-[(+)-2-(1-naphthylmethyl)-3-(phenethylcarbamoyl)propionyl]-L-histidine hydrazide in 2 ml of N,N-dimethylformamide were successively added 0.144 ml of a dry 5.1N-hydrogen chloride in N,N-dimethylformamide and 0.036 ml of isoamyl nitrite, and the mixture was stirred. After disappearance of hydrazide compound, the reaction mixture was cooled to −30° C., and the reaction mixture was neutralized by adding 0.102 ml of triethylamine to prepare a solution of N-[(+)-2-(1-naphthylmethyl)-3-

(phenethylcarbamoyl)propionyl]-L-histidine azide. The azide solution was added dropwise to a solution of 47 mg of (2RS,3S)-3-amino-2-hydroxy-5-methylhexanoyl-methylamide hydrochloride and 0.068 ml of triethylamine in 1 ml of N,N-dimethylformamide under ice-cooling, and the mixture was stirred for 16 hours under ice-cooling. A 5% aqueous sodium bicarbonate solution was added to the reaction mixture, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography eluent: chloroform/methanol=10/1 by volume) to obtain 65 mg of (2RS,3S)-3-{N-[(+)-2-(1-naphthylmethyl)-3-(phenethylcarbamoyl)propionyl]-L-histidyl}-amino-2-hydroxy-5-methylhexanoylmethylamide (a mixture of 2S and 2R forms) as a white powder.

Melting point: 105°–115° C. Rf$_1$: 0.50. MS: MH+, 655.

The racemic mixture obtained was purified by preparative silica gel thin layer chromatography (developing solvent: lower layer of chloroform/methanol/water=8/3/1 by volume) to obtain 17 mg of (3S)-3-{N-[(+)-2-(1-naphthylmethyl)-3-(phenethylcarbamoyl)-propionyl]-L-histidyl}amino-2-hydroxy-5-methylhexanoylmethylamide (isomer A) and 20 mg of it's isomer (isomer B).

Isomer A

Melting point: 110°–116° C. Rf$_1$: 0.51. Rf$_2$: 0.43. MS: MH+, 655.

Isomer B

Melting point: 115°–118° C. Rf$_1$: 0.49. Rf$_2$: 0.37. MS: MH+, 655.

EXAMPLE 6

(2RS,3S)-3{N-[(+)-2-(1-Napthylmethyl)-3-(phenethylcarbamoyl)propionyl]-L-histidyl}amino-2-hydroxy-5-methylhexanoyldimethylamide Dimethylamine gas was passed into a solution of 250 mg of (2RS,3S)-3-tert-butyloxycarbonylamino-2-hydroxy-5-methylhexanoic acid in 5 ml of dimethylformamide and 5 ml of tetrahydrofuran with stirring under ice-cooling, and 210 mg of 1-hydroxybenzotriazole and 221 mg of dicyclohexylcarbodiimide were added successively to the mixture. The mixture was stirred for 16 hours. The reaction mixture was evaporated under reduced pressure, and ethyl acetate was added to the residue. The mixture was cooled and precipitated crystals were filtered off. The ethyl acetate layer was washed with a 5% aqueous sodium bicarbonate solution, and a saturated sodium chloride aqueous solution, dried over anhydrous magnesium sulfate, and evaporated under reduced pressure. The residue was purified by silica gel flash column chromatography (eluent: chloroform) to obtain 130 mg of (2RS,3S)-3-tert-butyloxycarbonylamino-2-hydroxy-5-methylhexanoyldimethylamide as a colorless oil. [IR (neat): νco 1695, 1635 cm$^{-1}$].

A solution of 126 mg of the amide obtained in 10 ml of trifluoroacetic acid was stirred for 2 hours. The reaction mixture was evaporated under reduced pressure to obtain 140 mg of (2RS,3S)-3-amino-2-hydroxy-5-methylhexanoyldimethylamide.trifluoroacetic acid as a colorless oil. [IR (neat): νco 1635 cm$^{-1}$].

To a suspension of 170 mg of N-[(+)-2-(1-naphthylmethyl)-3-(phenethylcarbamoyl)propionyl]-L-histidine hydrazide in 10 ml of dry N,N-dimethylformamide were added successively 0.24 ml of a dry 5.1N-hydrogen chloride in N,N-dimethylformamide solution and 0.061 ml of isoamyl nitrite. After disappearance of hydrazide compound, the reaction mixture was cooled to −30° C., and the reaction mixture was neutralized by adding 0.17 ml of triethylamine to prepare a solution of N-[(+)-2-(1-naphthylmethyl)-3-(phenethylcarbamoyl)-propionyl]-L-histidine azide solution. The azide solution was added to a solution of 120 mg of (2RS,3S)-3-amino-2-hydroxy-5-methylhexanonyldimethylamide.-trifluoroacetic acid and 0.053 ml of triethylamine in 2 ml of dry N,N-dimethylformamide under ice-cooling, and the mixture was stirred for 16 hours under ice-cooling. The reaction mixture was evaporated under reduced pressure, and a 5% aqueous sodium bicarbonate solution was added to the residue. The mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol=15/1 by volume) to obtain 41 mg of (2RS,3S)-3-{N-[(+)-2-(1-naphthylmethyl)-3-(phenethylcarbamoyl)propionyl]-L-histidyl}amino-2-hydroxy-5-methylhexanoyldimethylamide as a white powder.

Melting point: 97°–102° C. Rf$_1$: 0.52. Rf$_2$: 0.43. MS: MH+, 669.

EXAMPLE 7

(2RS,3S)-3-{N-[(+)-2-(1-Naphthylmethyl)-3-(phenethylcarbamoyl)propionyl]-L-histidyl}amino-2-hydroxy-5-methylhexanoylisoamylamide To a solution of 261 mg of (2RS,3S)-3-tert-butyloxycarbonylamino-2-hydroxy-5-methylhexanoic acid and 0.21 ml of isoamylamine and 176 mg of 1-hydroxybenzotriazole in 2 ml of N,N-dimethylformamide and 2 ml of tetrahydrofuran was added 206 mg of dicyclohexylcarbodiimide with stirring under ice-cooling, and the mixture was stirred for 16 hours under ice-cooling. The reaction mixture was cooled and insoluble materials were filtered off. The filtrate was evaporated under reduced pressure, and the residue was dissolved in ethyl acetate. The ethyl acetate solution was washed successively with an aqueous citric acid solution, a 5% aqueous sodium bicarbonate solution and a saturated sodium chloride aqueous solution, dried over anhydrous magnesium sulfate, and evaporated under reduced pressure. The residue was purified by silica gel flash column chromatography (eluent: chloroform) to obtain 185 mg of (2RS,3S)-3-tert-butyloxycarbonylamino-2-hydroxy-5-methylhexanoylisoamylamide as a white powder. [IR (KBr: νco 1700, 1635 cm$^{-1}$].

To a solution of the amide obtained in 20 ml of methanol was 8 ml of a 2N-hydrochloric acid, and the mixture was heated at 60° C. for 1 hour. The reaction mixture was evaporated under reduced pressure to obtain 138 mg of (2RS,3S)-3-amino-2-hydroxy-5-methylhexanoylisoamylamide hydrochloride as a white powder. [IR (KBr): νco 1640 cm$^{-1}$].

To a solution of 130 mg of N-[(+)-2-(1-naphthylmethyl)-3-(phenethylcarbamoyl)propionyl]-L-histidine hydrazide in 3 ml of dry N,N-dimethylformamide were added successively 0.220 ml of a dry 5.1N-hydrogen chloride in N,N-dimethylformamide solution and 0.054 ml of isoamyl nitrite at −20° C., and the mixture was stirred. After disappearance of hydrazide compound, the reaction mixture was cooled to −30° C., and the reaction mixture was neutralized by 0.150 ml of triethylamine to prepare a solution of N-[(+)-2-(1-naphthylmethyl)-3-(phenethylcarbamoyl)propionyl]-L-histidine azide. The azide solution was added dropwise to a solution of 90 mg of (2RS,3S)-3-amino-2-hydroxy-5-methylhexanoylisoamylamide hydrochloride and 0.103 mg of triethylamine in 2 ml of dry N,N-dimethylformamide under ice-cooling, and the mixture was stirred for 16 hours under ice-cooling. A 5% aqueous sodium bicarbonate solution, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol 15/1 by volume) to obtain 19 mg of (2RS,3S)-3-{N-(+)-2-(1-naphthylmethyl)-3-(phenethylcarbamoyl)propionyl]-L-histidyl}amino-2-hydroxy-5-methylhexanoylisoamylamide as a white powder.

Melting point: 103°–107° C. $Rf_1$: 0.57. $Rf_2$: 0.54. MS: MH+, 711.

EXAMPLE 8

(2RS,3S)-3-{N-[(+)-2-(1-Naphthylmethyl)-3-(phenethylcarbamoyl)propionyl]-L-histidyl}amino-2-hydroxy-5-methylhexanoylbenzylamide To a solution of 155 mg of (2RS,3S)-3-tert-butyloxycarbonylamino-2-hydroxy-5-methylhexanoic acid and 85 mg of benzylamide in 5 ml of N,N-dimethylformamide and 5 ml of tetrahydrofuran was added successively 130 mg of 1-hydroxybenzotriazole and 137 mg of dicyclohexylcarbodiimide with stirring under ice-cooling, and the mixture was stirred for 16 hours under ice-cooling. The precipitated crystals were filtered off, and the filtrate was evaporated under reduced pressure. Ethyl acetate was added to the residue, and the mixture was cooled. The precipitates were filtered off. The ethyl acetate layer was washed successively with a 5% aqueous sodium bicarbonate solution and a saturated sodium chloride aqueous solution, dried over anhydrous magnesium sulfate, and evaporated under reduced pressure. The residue was purified by preparative silica gel thin layer chromatography (developing solvent: chloroform/methanol=20/1 by volume) to obtain 192 mg of (2RS,3S)-3-tert-butyloxycarbonylamino-2-hydroxy-5-methylhexanoylbenzylamide as a colorless viscous oil. [IR (neat): υco 1680, 1640 cm−1].

A solution of 190 mg of the amide obtained in 10 ml of trifluoroacetic acid was stirred for 3 hours at room temperature. The reaction mixture was evaporated under reduced pressure to obtain 191 mg of (2RS,3S)-3-amino-2-hydroxy-5-methylhexanoylbenzylamide.trifluoroacetic acid as a yellow viscous oil. [IR (neat): υco 1650 cm−1].

To a suspension of 120 mg of N-[(+)-2-(1-naphthylmethyl)-3-(phenethylcarbamoyl)propionyl]-L-histidine hydrazide in 7 ml of N,N-dimethylformamide was added successively 0.16 ml of a dry 5.1N-hydrogen chloride in N,N-dimethylformamide solution and 0.04 ml of isoamyl nitrite at −20° C. with stirring. After disappearance of hydrazide compound, the reaction mixture was cooled to −30° C., and the mixture was neutralized by adding 0.11 ml of triethylamine to prepare a solution of [(+)-2-(1-naphthylmethyl)-3-(phenethylcarbamoyl)propionyl]-L-histidine azide solution. The azide solution was added dropwise to a solution of 86 mg of (2RS, 3S)-3-amino-2-hydroxy-5-methylhexanoylbenzylamide.trifluoroacetic acid and 0.034 ml of triethylamine in 2 ml of N,N-dimethylformamide under ice-cooling, and the mixture was stirred for 16 hours under ice-cooling. The reaction mixture was evaporated under reduced pressure. The residue was washed successively with a 5% aqueous sodium bicarbonate solution, dried over anhydrous magnesium sulfate, and evaporated under reduced pressure. The residue was purified by silica gel flash column chromatography (eluent:chloroform/methanol=15/1 by volume) to obtain 62 mg of (2RS, 3S)-3-{N-[(+)-2-(1-naphthylmethyl)-3-(phenethylcarbamoyl)propionyl]-L-histidyl-}amino-2-hydroxy-5-methylhexanoylbenzylamide as a white powder.

Melting point: 101°–106° C. $Rf_1$: 0.60. $Rf_2$: 0.50. MS: MH+, 731.

EXAMPLE 9

N-[(+)-2-(1-Naphthylmethyl)-3-(phenethylcarbamoyl)propionyl]-L-histidylstatylmethylamide To a solution of 100 mg of N-(tert-butyloxycarbonyl)statine (commerically available) and 0.05 ml of a 30% aqueous methylamine in 3 ml of N,N-dimethylformamide and 3 ml of tetrahydrofuran were added successively 79 mg of 1-hydroxybenzotriazole and 83 mg of dicyclohexylcarbodiimide, and the mixture was stirred for 16 hours. The reaction mixture was evaporated under reduced pressure and ethyl actate was added to the residue. The mixture was cooled and the precipitated crystals were filtered off. The ethyl acetate layer was washed successively with a 5% aqueous sodium bicarbonate solution and a saturated sodium chloride aqueous solution, dried over anhydrous magnesium sulfate, and evaporated under reduced pressure. The residue was purified by silica gel flash column chromatography (eluent:chloroform/methanol=40/1 by volume) to obtain 110 mg of N-(tert-butyloxycarbonyl)-statinemethylamide as a colorless viscous oil. [IR (neat): υco 1680, 1630 cm−1].

A solution of 105 mg of the amide obtained in 10 ml of trifluoroacetic acid was stirred for 3.5 hours at room temperature. The reaction mixture was evaporated under reduced pressure to obtain 122 mg of statylmethylamide.trifluoroacetic acid as a colorless viscous oil. [IR (neat): υco 1650 cm−1].

To a suspension of 140 mg of N-[(+)-2-(1-naphthylmethyl)-3-(phenethylcarbamoyl)propionyl]-L-histidine hydrazide in 8 ml of dry N,N-dimethylformamide were added successively 0.19 ml of a dry 5.1N-hydrogen chloride in N,N-dimethylformamide solution and 0.048 ml of isoamyl nitrite at 31 20° C. with stirring. After a disappearance of hydrazide compound, the reaction mixture was cooled −30° C., the reaction mixture was neutralized by adding 0.14 ml of triethylamine to prepare a solution of N-[(+)-2-(1-naphthylmethyl)-3-(phenethylcarbamoyl)propionyl]-L-histidine azide. The azide solution was added dropwise to a solution of 90 mg of statylmethylamide.trifluoroacetic acid and 0.04 ml of triethylamine in dry N,N-dimethylformamide under ice-cooling, and the mixture was stirred for 16 hours. The reaction mixture was evaporated under reduced pressure. A 5% aqueous sodium bicarbonate solution was added to the residue, and the mixture was extracted with ethyl acetate. The ethyl acetate layer was washed with a saturated sodium chloride aqueous solution, dried over anhydrous magnesium sulfate, and evaporated under reduced pressure. The residue was purified by a silica gel flash column chromatography (eluent:chloroform/methanol=15/1 by volume) to obtain 22 mg of N-[(+)-2-(1-naphthylmethyl)-3-phenethylcarbamoyl)propionyl]-L-histidyl-statylmethylamide as a white powder.

Melting point: 101°–107° C. Rf$_1$: 0.54. Rf$_2$: 0.44. MS: MH+, 669.

EXAMPLE 10

N-[(+)-2-(1-Naphthylmethyl)-3-(phenethylcarbamoyl)-propionyl]-L-histidylstatylisoamylamide To a solution of 100 mg of N-(tert-butyloxycarbonyl)statine (commerically available) and 42 mg of isoamylamine in 3 ml of N,N-dimethylformamide and 3 ml of tetrahydrofuran were added successively dropwise 79 mg of 1-hydroxybenzotriazole and 83 mg of dicyclohexylcarbodiimide, and the mixture was stirred for 16 hours under ice-cooling. The reaction mixture was evaporated under reduced pressure, and ethyl acetate was added to the residue. The mixture was cooled and then the precipitated crystal were filtered off. The ethyl acetate layer was washed successively with a 5% aqueous sodium bicarbonate solution and a saturated sodium chloride aqueous solution, dried over anhydrous magnesium sulfate, and evaporated under reduced pressure. The residue was purified by silica gel flash column chromatography (eluent:chloroform/methanol=40/1 by volume) to obtain 132 mg of N-(tert-butyloxycarbonyl)statylisoamylamide as a colorless viscous oil. [IR (neat): νco 1685, 1640 cm$^{-1}$].

A solution of 130 mg of the amide obtained in 10 ml of trifluoroacetic acid was stirred for 3 hours at room temperature. The reaction mixture was evaporated under reduced pressure to obtain 132 mg of statylisoamylamide.trifluoroacetic acid as a colorless viscous oil. [IR (neat): νco 1665 cm$^{-1}$].

To a suspension of 164 mg of N-[(+)-2-(1-naphthylmethyl)-3-(phenethylcarbamoyl)propionyl]-L-histidine hydrazide in 10 ml of dry N,N-dimethylformamide were added successively a solution of 0.21 ml of a dry 5.1N-hydrogen chloride in N,N-dimethylformamide solution and 0.051 ml of isoamyl nitrite under ice-cooling, and the mixture was stirred. After disappearance of hydrazide compound, the reaction mixture was cooled to −30° C., and neutralized by adding 0.15 ml of triethylamine to prepare a solution of N-[(+)-2-(1-naphthylmethyl)-3-(phenethylcarbamoyl)propionyl]-L-histidine azide. The azide solution prepared was added dropwise to a solution of 115 mg of statylisoamylamide.trifluoroacetic acid and 0.045 ml of triethylamine in 2 ml of dry N,N-dimethylformamide under ice-cooling, and the mixture was stirred for 16 hours under ice-cooling. The reaction mixture was evaporated under reduced pressure. A 5% aqueous sodium bicarbonate solution was added to the residue, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent:chloroform/methanol=15/1 by volume) to obtain 51 mg of N-[(+)-2-(1-naphthylmethyl)-3-(phenethylcarbamoyl)propionyl]-L-histidylstatylisoamylamide as white powder.

Melting point: 92°–97° C. Rf$_1$: 0.61. Rf$_2$: 0.51. MS: MH+, 725.

EXAMPLE 11

(2RS, 3S)-3-{N-(+)-2-(1-Naphthylmethyl)-3-(phenethylcarbamoyl)propionyl]-L-histidyl}amino-2-hydroxy-5-methylhexyl methyl ether To a solution of 176 mg of (3S)-3-carbobenzoxyamino-5-methyl-1,2-epoxyhexane in 10 ml of methanol was added 2 g of dry neutral alumina, and the mixture was heated under reflux for 16 hours. After filtration of the alumina, the filtrate was evaporated under reduced pressure. The residue was purified by preparative silica gel thin layer chromatography (developing solvent: lower layer of chloroform/methanol/water=8/3/1 by volume) to obtain 96 mg of (2RS, 3S)-3-carbobenzoxyamino-2-hydroxy-5-methylhexyl methyl ether as a colorless viscous oil.

To a solution of 94 mg of the ether compound obtained in 10 ml of methanol was added 0.16 ml of a 2N-hydrochloric acid, and the mixture was hydrogenated over 10 mg of a 10% palladium charcoal under hydrogen atmosphere. After filtration of the catalyst, the filtrate was evaporated under reduced pressure to obtain 54 mg of (2RS, 3S)-3-amino-2-hydroxy-5-methylhexyl methyl ether hydrochloride as a colorless viscous oil.

To a suspension of 130 mg of N-[(+)-2-(1-naphthylmethyl)-3-(phenethylcarbamoyl)propionyl]-L-histidine hydrazide in 6 ml of dry N,N-dimethylformamide were added successively dropwise 0.19 ml of a dry 5.1N-hydrogen chloride in N,N-dimethylformamide solution and 0.05 ml of isoamyl nitrite, and the mixture was stirred. After disappearance of hydrazide compound, the reaction mixture was cooled to −30° C., and neutralized by adding 0.14 ml of triethylamine to prepare a solution of N-[(+)-2-(1-naphthylmethyl)-3-(phenethylcarbamoyl)propionyl]-L-histidine azide. The azide solution prepared was added drowise to a solution of 52 mg of (2RS, 3S)-3-amino-2-hydroxy-5-methylhexyl methyl ether hydrochloride and 0.05 ml of triethylamine in 2 ml of dry N,N-dimethylformamide under ice-cooling, and the mixture was stirred for 16 hours under ice-cooling. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by preparative silica gel thin layer chromatography (developing solvent: lower layer of chloroform/methanol/water32 8/3/1 by volume) to obtain 55 mg of (2RS, 3S)-3-{N-[(+)-2-(1-naphthylmethyl)-3-(phenethylcarbamoyl)propionyl]-L-histidyl}-amino-2-hydroxy-5-methylhexyl methyl ether as a white powder.

Melting point: 91°–95° C. Rf$_1$: 0.60. Rf$_2$: 0.40. MS: MH+, 642.

EXAMPLE 12

(2RS, 3S)-3-{N-[(+)-2-(1-Naphthylmethyl)-3-(phenethylcarbamoyl)propionyl]-L-histidyl}amino-2-hydroxy-5-methylhexyl isoamyl ether A mixture of 100 mg of (3S)-3-carbobenzoxyamino-5-methyl-1,2-epoxyhexane, 2 g of dry neutral alumina, and 2 ml of isoamyl alcohol was stirred for 16 hours at 100° C., and then stirred for 90 minutes at 140° C. After filtration of the alumina, the filtrate was evaporated under reduced pressure to obtain 97 mg of (2RS, 3S)-3-carbobenzoxyamino-2-hydroxy-5-methylhexyl isoamyl ether as a colorless oil.

To a solution of 95 mg of the ether obtained in 2 ml of methanol was added 0.27 ml of a 1N-hydrochloric acid, and the mixture was hydrogenated over 10 mg of a 10% palladium charcoal under hydrogen atmosphere. After filtration of the catalyst, the filtrate was evaporated under reduced pressure to obtain 65 mg of (2RS, 3S)-3-amino-2-hydroxy-5-methylhexyl isoamyl ether hydrochloride as a colorless viscous oil.

To a solution of 115 mg of N-[(+)-2-(1-naphthylmethyl)-3-(phenethylcarbamoyl)propionyl]-L-histidine hydrazide in 2 ml of N,N-dimethylformamide were added successively dropwise 0.16 ml of a dry 5.1N-hydrogen chloride in N,N-dimethylformamide solution and 0.04 ml of isoamyl nitrite under ice-cooling, and mixture was stirred. After disappearance of hydrazide compound, the reaction mixture was cooled to −30° C., and neutralized by adding 0.11 ml of triethylamine to prepare a solution of N-[(+)-2-(1-naphthylmethyl)-3-(phenethylcarbamoyl)propionyl]-L-histidine azide. The azide solution was added dropwise to a solution of 63 mg of (2RS, 3S)-3-amino-2-hydroxy-5-methylhexyl isoamyl ether and 0.035 ml of triethylamine in 2 ml of N,N-dimethylformamide solution under ice-cooling, and the mixture was stirred for 16 hours under ice-cooling. A 5% aqueous sodium bicarbonate solution was added to the reaction mixture, and the mixture was extracted with ethyl acetate. The ethyl acetate layer was washed with a saturated sodium chloride aqueous solution, dried over magnesium sulfate, and evaporated under reduced pressure. The residue was purified by preparative silica gel thin layer chromatography (developing solvent: lower layer of chloroform/methanol/water 8/3/1 by volume) to obtain 51 mg of (2RS, 3S)-3-{N-[(+)-2-(1-naphthylmethyl)-3-(phenethylcarbamoyl)-propionyl]-L-histidyl}amino-2-hydroxy-5-methylhexyl isoamyl ether as a white powder.

Melting point: 73°–76° C. Rf$_1$: 0.63. Rf$_2$: 0.57. MS: MH+, 698.

EXAMPLE 13

(2RS, 3S)-3-{N-[(+)-2-(1-naphthylmethyl)-3-phenethylcarbamoyl)propionyl]-L-histidyl}amino-2-hydroxy-5-methylhexyl benzyl ether A mixture of 100 mg of (3S)-3-carbobenzoxyamino-5-methyl-1,2-epoxyhexane, 2 g of dry silica gel and 2 ml of benzyl alcohol was heated at 100° C. for 16 hours. After filtration of the silica gel, the filtrate was evaporated under reduced pressure to obtain 105 mg of (2RS, 3S)-3-carbobenzoxyamino-2-hydroxy-5-methylhexyl benzyl ether as a colorless oil. To a solution of 86 mg of the ether obtained in 10 ml of methanol was added 0.14 ml of a 2N-hydrochloric acid, and the mixture was hydrogenated over 17 mg of palladium charcoal under hydrogen atmosphere. After filtration of the catalyst, the filtrate was evaporated under reduced pressure. The residue was purified by preparative silica gel thin layer chromatography (developing solvent: lower layer of chloroform/methanol/water=8/3/1 by volume) to obtain 17 mg of (2RS, 3S)-3-amino-2-hydroxy-5-methylhexyl benzyl ether hydrochloride as a colorless viscous oil.

To a suspension of 31 mg of N-[(+)-2-(1-naphthylmethyl)-3-(phenethylcarbamoyl)propionyl]-L-histidine hydrazide in 1 ml of N,N-dimethylformamide were added successively dropwise 0.044 ml of a dry 5.1N-hydrogen chloride in N,N-dimethylformamide solution and 0.011 ml of isoamyl nitrite, and the mixture was stirred. After disappearance of hydrazide compound, the reaction mixture was cooled to +30° C., and neutrlized by adding 0.031 ml of triethylamine to prepare a solution of N-[(+)-2-(1-naphthylmethyl)-3-(phenethylcarbamoyl)-propionyl]-L-histidine azide. The azide solution prepared was added dropwise to a solution of 16 mg of (2RS, 3S)-3-amino-2-hydroxy-5-methylhexyl benzyl ether hydrochloride and 0.011 ml of triethylamine in 1 ml of N,N-dimethylformamide under ice-cooling, and the mixture was stirred for 16 hours under ice-cooling. A 5% aqueous sodium bicarbonate solution was added to the reaction mixture, and the mixture was extracted with ethyl acetate. The ethyl acetate layer was washed with a saturated sodium chloride aqueous solution, dried over anhydrous magnesium sulfate, and evaporated under reduced pressure. The residue was purified by preparative silica gel thin layer chromatograpy (developing solvent: lower layer of chloroform/methanol/water=8/3/1 by volume) to obtain 18 mg of (2RS, 3S)-3-{N-(+)-2-(1-naphthylmethyl)-3-(phenethylcarbamoyl)propionyl]-L-histidyl}amino-2-hydroxy-5-methylhexyl benzyl ether as a white powder.

Melting point: 76°–79° C. Rf$_1$: 0.61. Rf$_2$: 0.55. MS: MH+, 718.

EXAMPLE 14

(2RS, 3S)-N-Isoamyl-3-{N-[(+)-2-(1-naphthylmethyl)-3-(phenethylcarbamoyl)propionyl]-L-histidyl}-amino-2-hydroxy-5-methylhexylamine A mixture of 50 mg of (3S)-3-carbobenzoxyamino-5-methyl-1,2-epoxyhexane, 0.5 g of dry neutral alumina and 1 ml of isoamylamine was stirred for 16 hours at room temperature, and heated at 70° C. for 90 minutes. After filtration of the alumina, the filtrate was evaporated under reduced pressure to obtain 71 mg of (2RS, 3S)-N-isoamyl-3-carbabenzoxyamino-2-hydroxy-5-methylhexyamine as a colorless oil. To a solution of 70 mg of the amine obtained in 2 ml of methanol was added 0.2 ml of a 2N-hydrochloric acid, and the mixture was hydrogenated over 7 mg of palladiumcharcoal under hydrogen atmosphere. After filtration of the catalyst, the filtrate was evaporated under reduced pressure to obtain 42 mg of (2RS, 3S)-N-isoamyl-3-amino-2-hydroxy-5-methylhexylamine dihydrochloride as a colorless viscous oil.

To a solution of 64 mg of N-[(+)-2-(1-naphthylmethyl)-3-(phenethylcarbamoyl)propionyl]-L-histidine hydrazide in 2 ml of N,N-dimethylformamide were added successively dropwise 0.09 ml of a dry 5.1N-hydrogen chloride in N,N-dimethylformamide solution and 0.022 ml of isoamyl nitrite at −20° C., and the mixture was stirred under ice-cooling. After disappearance hydrazide compound, the reaction mixture was cooled to −30° C., and neutralized by adding 0.063 ml of triethylamine to prepare a solution of N-[(+)-2-(1-naphthylmethyl)-3-(phenethylcarbamoyl)-propionyl]--histidine azide. The azide solution was added dropwise to a solution of 40 mg of (2RS, 3S)-N-isoamyl-3-amino-2-hydroxy-5-methylhexylamine dihydrochloride in 2 ml of N,N-dimethylformamide under ice-cooling, and the mixture was stirred for 16 hours under ice-cooling. A 5% aqueous sodium bicarbonate solution was added to the reaction mixture, and the mixture was extracted with ethyl acetate. The ethyl acetate layer was washed with a saturated sodium chloride aqueous solution, dried over anhydrous magnesium sulfate, and evaporated under reduced pressure. The residue was purified by preparative silica gel thin layer chromatography (developing solvent: lower layer of chloroform/methanol/water=8/3/1 by volume) to obtain 8 mg of (2RS, 3S)-N-isoamyl-3-{N-[(+)-2-(1-naphthylmethyl)-3-(phenethylcarbamoyl)propionyl]-L-histidyl}amino-2-hydroxy-5-methylhexylamine as a white powder.

Melting point: 92°–97° C. $Rf_1$: 0.10. $Rf_2$: 0.04. MS: $MH^+$, 697.

EXAMPLE 15

(2RS, 3S)-N-Benzyl-3-{N-[(+)-2-(1-naphthylmethyl)-3-(phenethylcarbamoyl)propiobnyl]-L-histidyl}amino-2-hydroxyl-5-methylhexylamine To a solution of 100 mg of (3S)-3-carbobenzoxyamino-5-methyl-1,2-epoxyhexane in 10 ml of diethyl ether were added 2 g of dry silica gel and 0.1 ml of benzylamine, and the mixture was stirred for 16 hours at room temperature, then heated under reflux for 2 hours. After filtration of the silica gel, the filtrate was evaporated under reduced pressure. The residue was purified by preparative silica gel thin layer chromatography (developing solvent: lower layer of chloroform/methanol/water=8/3/1 by volume) to obtain 56 mg of (3S)-N-benzyl-3-carbobenzoxyamino-2-hydroxy-5-methylhexylamine as a colorless viscous oil. To a solution of 54 mg of the amine compound obtained in 10 ml methanol was added 0.2 ml of a 2N-hydrochloric acid. The mixture was hydrogenated over 10 mg of palladium charcoal under hydrogen atmosphere. After filtration of the catalyst, the filtrate was evaporated under reduced pressure to obtain 43 mg of (3S)-N-benzyl-3-amino-2-hydroxy-5-methylhexylamine dihydrochloride.

To a suspension of 66 mg of N-[(+)-2-(1-naphthylmethyl)-3-(phenethylcarbamoyl)propionyl]-L-histidine hydrazide in 5 ml of dry N,N-dimethylformamide were added successively 0.08 ml of a dry 5.1N-hydrogen chloride in N,N-dimethylformamide solution and 0.02 ml of isoamyl nitrite at −20° C. with stirring, and the mixture was stirred under ice-cooling. After disappearance of hydrazide compound, the reaction mixture was cooled to −30° C., and neutralized by adding 0.06 ml of triethylamine to prepare a solution of N-[(+)-2-(1-naphthylmethyl)-3-(phenethylcarbamoyl)propionyl]-L-histidine azide. The azide solution was added dropwise to a solution of 40 mg of (3S)-N-benzyl-3-amino-2-hydroxy-5-methylhexylamine dihydrochloride and 0.018 ml of triethylamine in 2 ml of dry N,N-dimethylformamide under ice-cooling, and the mixture was stirred for 16 hours under ice-cooling. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol=15/1 by volume) to obtain 33 mg of (2RS, 3S)-N-benzyl-3-{N-[(+)-2-(1-naphthylmethyl)-3-(phenethylcarbamoyl)propionyl]-L-histidyl}amino-2-hydroxy-5-methylhexylamine as a white powder.

Melting point: 108°–113° C. $Rf_1$: 0.44. $Rf_2$: 0.14. MS: $MH^+$, 717.

EXAMPLE 16

(2RS, 3S)-3-{N-[(+)-2-(1-naphthylmethyl)-3-(phenethylcarbamoyl)propionyl]-L-histidyl}amino-2-hydroxy-5-methylhexanol Hydrogen chloride was passed into a solution of 110 mg of (2RS, 3S)-3-amino-2-hydroxy-5-methylhexanoic acid in 10 ml of methanol with stirring, and the mixture was stirring overnight, and the mixture was evaporated to dryness under reduced pressure to obtain 150 mg of methyl (2RS, 3S)-3-amino-2-hydroxy-5-methylhexanoate hydrochloride as a white powder. [IR (KBr): $\nu$co 1740 cm$^{-1}$].

To a solution of 154 mg of N-[(+)-2-(1-naphthylmethyl)-3-(phenethylcarbamoyl)propionyl]-L-histidine hydrazide in 4 ml of N,N-dimethylformamide were added successively dropwise 0.19 ml of a dry 5.1N-hydrogen chloride in N,N-dimethylformamide solution and 0.05 ml of isoamyl nitrite at −20° C., and the mixture was stirred. After disapperance of hydrazide compound, the reaction mixture was cooled to −30° C., and neutralized by adding 0.14 ml of triethylamine to prepare a solution of N-[(+)-2-(1-naphthylmethyl)-3-(phenethylcarbamoyl)propionyl]-L-histidine azide. The azide solution prepared was added dropwise to a solution of 64 mg of methyl (2RS, 3S)-3-amino-2-hydroxy-5-methylhexanoate hydrochloride and 0.09 ml of triethylamine in 2 ml of N,N-dimethylformamide under ice-cooling, and the mixture was stirred for 16 hours under ice-cooling. A 5% aqueous sodium bicarbonate solution was added to the reaction mixture, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol=10/1 by volume) to obtain 120 mg of methyl (2RS, 3S)-3-{N-[(+)-2-(1-naphthylmethyl)-3-(phenethylcarbamoyl)propionyl]-L-histidyl}amino-2-hydroxy-5-methylhexanoate as a white powder.

Melting point: 82°–87° C. $Rf_1$: 0.58. MS: $MH^+$, 656. To a solution of 37 mg of the methyl ester compound obtained in 8 ml of ethanol and 2 ml of water was added 22 mg of sodium borohydride under ice-cooling, and the mixture was stirred for 16 hours at room temperature. The reaction mixture was evaporated under reduced pressure, and ethyl acetate was added to the residue. The mixture was washed successively with a 5% aqueous sodium bicarbonate solution and a saturated sodium chloride aqueous solution, dried over anhydrous magnesium sulfate, and evaporated under reduced pressure to obtain 25 mg of (2RS, 3S)-3-{N-[(+)-2-(1-naphthylmethyl)-3-(phenethylcarbamoyl)propionyl]-L-histidyl}amino-2-hydroxy-5-methylhexanol as a white powder.

Melting point: 101°–107° C. $Rf_1$: 0.44. $Rf_2$: 0.15. MS: $MH^+$, 536.

EXAMPLE 17

(3S, 4S)-4-{N-[(+)-2-(1-naphthylmethyl)-3-(phenethylcarbamoyl)propionyl]-L-histidyl}amino-3-hydroxy-6-methylheptanol Hydrogen chloride was passed into a solution of 100 mg of N-(tert-butyloxycarbonyl)statine (commercially available) with stirring under ice-cooling, and the mixture was stirred overnight at room temperature. The reaction mixture was evaporated under reduced pressure to obtain 81 mg of statine methyl ester hydrochloride as a colorless viscous oil. [IR (neat): νco 1725 cm$^{-1}$].

To a suspension of 180 mg of N-[(+)-2-(1-naphthylmethyl)-3-(phenethylcarbamoyl)propionyl]-L-histidine hydrazide in 10 ml of dry N,N-dimethylformamide were added successively dropwise 0.24 ml of a dry 5.1N-hydrogen chloride in N,N-dimethylformamide solution and 0.06 ml of isoamyl nitrite at −20° C. with stirring and mixture was stirred under ice-cooling. After disappearance of hydrazide compound, the reaction mixture was cooled to −30° C., and neutralized by adding 0.16 ml of triethylamine to prepare a solution of N-[(+)-2-(1-naphthylmethyl)-3-(phenethylcarbamoyl)propionyl]-L-histidine azide. The azide solution prepared was added dropwise to a solution of 80 mg of statine methyl ester hydrochloride and 0.06 ml of triethylamine in 2 ml of dry N,N-dimethylformamide under ice-cooling, and the mixture was stirred for 16 hours under ice-cooling. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol 15/1 by volume) to obtain 35 mg of methyl N-[(+)-2-(1-naphthylmethyl)-3-(phenethylcarbamoyl)-propionyl]-L-histidiylstatinate as a white powder.

Melting point: 90°-94° C. Rf$_1$: 0.67 Rf$_2$: 0.65 MS: MH+, 670.

To a solution of 25 mg of methyl statinate in 8 ml of ethanol and 2 ml of water was added 14 mg of sodium borohydride under ice-cooling, and the mixture was stirred for 16 hours at room temperature. The reaction mixture was evaporated under reduced pressure, and ethyl acetate was added to the residue. The mixture was washed successively with a 5% aqueous sodium bicarbonate solution and a saturated sodium chloride aqueous solution, dried over anhydrous magnesium sulfate, and evaporated under reduced pressure to obtain 7 mg of (3S, 4S)-4-{N-[(+)-2-(1-naphthylmethyl)-3-(phenethylcarbamoyl)propionyl]-L-histidyl}amino-3-hydroxy-6-methylheptanol as a white powder.

Melting point: 87°-92° C. Rf$_1$: 0.53 Rf$_2$: 0.25 MS: MH+, 642

TEST EXAMPLE 1

Human renin-sheep renin substrate reaction system in vitro

To a mixture containing 200 μl of a 125 mM pyrophosphate buffer (ph 7.4), 25 μl of a 20 mM aqueous solution of L-phenylalanyl-L-alanyl-L-proline as an angiotensin converting enzyme inhibitor, 50 μl of semipurified sheep renin substrate (4400 ng angiotensin I/ml) 50 μl of dimethyl sulfoxide solution of a dipeptide of the present invention and 150 μl of deionized water was added 25 μl of purified human renin (20-30 ng angiotensin I/hr). The mixture was incubated for 15 minutes on a water bath at 37° C., and the reaction mixture was allowed to stand for 5 minutes on a water bath at 100° C. to stop the reaction. After cooling, 200 μl of the solution were taken up and the amount of angiotensin I produced by the addition of renin was determined by radioimmunoassay. The inhibitory effect was calculated by the following equation.

Inhibition (%) =

$$\frac{\text{Amount of angiotensin I in control} - \text{Amount of angiostensin I in a mixture containing a compound of this invention}}{\text{Amount of angiotensin I in control}} \times 100$$

As a control, the same procedure as above was carried out by using 50 μl of dimethyl sulfoxide alone in place of the 50 μl of dimethyl sulfoxide solution containing an amino acid derivative of the present invention.

The molar concentration which produced 50% inhibition (IC$_{50}$) was calculated from the inhibition value obtained, and the results are shown below.

| Compound | IC$_{50}$ (molar concentration) |
| --- | --- |
| Methyl (2RS, 3S)-3-{N—[(+)-2-(1-naphthylmethyl)-3-(phenethylcarbamoyl)propionyl]-L-Histidyl}amino-2-hydroxy-5-methylhexanoate [mixture of (2S, 3S) form and (2R, 3S) form in the ratio of 3:7] | 4.9 × 10$^{-8}$ |
| Methyl (2S, 3S)-3-{N—[(+)-2-(1-naphthylmethyl)-3-(phenethylcarbamoyl)propionyl]-L-histidyl}-amino-2-hydroxy-5-methylhexanoate | 1.3 × 10$^{-6}$ |
| Methyl (2R, 3S)-3-{N—[(+)-2-(1-naphthylmethyl)-3-(phenethylcarbamoyl)propionyl]-L-histidyl}-amino-2-hydroxy-5-methylhexanoate | 3.1 × 10$^{-8}$ |
| Isoamyl (2RS, 3S)-3-{N—[(+)-2-(1-naphthylmethyl)-3-(phenethylcarbamoyl)propionyl]-L-histidyl}-amino-2-hydroxy-5-methylhexanoate | 6.1 × 10$^{-8}$ |
| Benzyl (2RS, 3S)-3-{N—[(+)-2-(1-naphthylmethyl)-3-(phenethylcarbamoyl)propionyl]-L-histidyl}-amino-2-hydroxy-5-methylhexanoate | 4.2 × 10$^{-8}$ |
| Methyl N—(+)-2-(1-naphthylmethyl)-3-(phenethylcarbamoyl)-propionyl]-L-histidylstatinate | 3.1 × 10$^{-7}$ |
| (2RS, 3S)-3-{N—[(+)-2-(1-Naphthylmethyl)-3-(phenethylcarbamoyl)-propionyl]-L-histidyl}amino-2-hydroxy-5-methylhexanoylmethyl amide (racemic mixture) | 7.0 × 10$^{-7}$ |
| (3S)-3-{N—[(+)-2-(1-Naphthylmethyl)-3-(phenethylcarbamoyl)-propionyl]-L-histidyl}amino-2-hydroxy-5-methylhexanoylmethyl amide (isomer A) | 4.5 × 10$^{-6}$ |
| (3S)-3-{N—[(+)-2-(1-naphthylmethyl)-3-(phenethylcarbamoyl)-propionyl]-L-histidyl}amino-2-hydroxy-5-methylhexanoylmethyl amide (isomer B) | 3.9 × 10$^{-7}$ |
| (2RS, 3S)-3-{N—[(+)-2-(1-Naphthylmethyl)-3-(phenethylcarbamoyl)-propionyl]-L-histidyl}amino-2-hydroxy-5-methylhexanoyl- | 2.8 × 10$^{-6}$ |

-continued

| Compound | IC$_{50}$ (molar concentration) |
|---|---|
| dimethylamide | |
| (2RS, 3S)-3-{N—[(+)-2-(1-Naphthyl-methyl)-3-(phenethylcarbamoyl)-propionyl]-L-histidyl}amino-2-hydroxy-5-methylhexanoyl-isoamylamide | $2.5 \times 10^{-7}$ |
| (2RS, 3S)-3-{N—[(+)-2-(1-Naphthyl-methyl)-3-(phenethylcarbamoyl)-propionyl]-L-histidyl}amino-2-hydroxy-5-methylhexanoyl-benzylamide | $1.0 \times 10^{-7}$ |
| N—[(+)-2-(1-Naphthylmethyl)-3-(phenethylcarbamoyl)propionyl]-L-histidylstatinemethylamide | $7.4 \times 10^{-7}$ |
| N—[(+)-2-(1-Naphthylmethyl)-3-(phenethylcarbamoyl)propionyl]-L-histidylstatineisoamylamide | $7.2 \times 10^{-8}$ |
| (2RS, 3S)-3-{N—[(+)-2-(1-Naphthylmethyl)-3-(phenethylcarbamoyl)propionyl]-L-histidyl}-amino-2-hydroxy-5-methylhexyl methyl ether | $7.9 \times 10^{-7}$ |
| (2RS, 3S)-3-{N—[(+)-2-(1-Naphthylmethyl)-3-(phenethylcarbamoyl)propionyl]-L-histidyl}-amino-2-hydroxy-5-methylhexyl isoamyl ether | $2.8 \times 10^{-7}$ |
| (2RS, 3S)-3-{N—[(+)-2-(1-Naphthylmethyl)-3-(phenethylcarbamoyl)propionyl]-L-histidyl}-amino-2-hydroxy-5-methylhexyl benzyl ether | $4.7 \times 10^{-7}$ |
| (2RS, 3S)-N—Isoamyl-3-{N—[(+)-2-(1-naphthylmethyl)-3-(phenethylcarbamoyl)propionyl]-L-histidyl}amino-2-hydroxy-5-methylhexylamine | $3.5 \times 10^{-7}$ |
| (2RS, 3S)-N—Benzyl-3-{N—[(+)-2-(1-naphthylmethyl)-3-(phenethylcarbamoyl)propionyl]-L-histidyl}amino-2-hydroxy-5-methylhexylamine | $1.5 \times 10^{-7}$ |
| (2RS, 3S)-3-{N—[(+)-2-(1-naphthylmethyl)-3-(phenethylcarbamoyl)propionyl]-L-histidyl}-amino-2-hydroxy-5-methylhexanol | $5.9 \times 10^{-7}$ |
| (3S, 4S)-4-{N—[(+)-2-(1-naphthylmethyl)-3-(phenethylcarbamoyl)-propionyl]-L-histidyl}amino-3-hydroxy-6-methylheptanol | $5.9 \times 10^{-6}$ |

TEST EXAMPLE 2

Hypotensive effect in marmoset

The experiment was carried out by using common marmoset as described in K. G. Hofbauer et al., Clinical and Experimental Hypertension-Theory and Practice, Vol. A5, No. 7 & 8 (1983), pages 1237–1247.

Furosemide was orally administered three times to common marmoset at 15 mg per kilogram per day every other day to create a high renin state. Blood pressure of consious marmoset was measured 2 days after the last administration of furosemide.

Measurement of blood pressure

Male common marmoset weighing 325 g was lightly anesthetized by ketamine hydrochloride (Ketalar, produced by Parke Davis, 20 mg/kg i.m.), and their carotid artery and vein exposed.. Catheters being filled with a heparin solution was subcutaneously inserted into the carotid artery and vein from the dorsum. After suturing of the opened part, the marmosets were placed on a heated mat. After complete recovery from the anesthesia, an amino acid derivative of the present invention (2.5 mg/kg) was intravenously injected through the venous catheter.

The arterial catheter was connected to a pressure transducer and blood pressure was recorded on the polygraph. The results are shown below.

TABLE

| Compound: Methyl (2RS, 3S)-3-{N—[(+)-2-(1-naphthyl-methyl)-3-(phenethylcarbamoyl)propionyl]-L-histidyl}amino-2-hydroxy-5-methylhexanoate ||| 
|---|---|---|
| Time after injection (min) | Systolic blood pressure (mm Hg) | Diastolic blood pressure (mm Hg) |
| Control | 103 | 72 |
| 1 | 85 | 56 |
| 3 | 91 | 61 |
| 5 | 92 | 62 |
| 10 | 102 | 70 |
| 15 | 103 | 72 |

What is claimed is:

1. An amino acid derivative represented by formula (I):

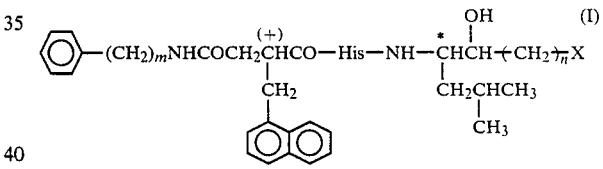

wherein X represents a straight or branched chain alkoxycarbonyl group having 2 to 10 carbon atoms, or aralkoxycarbonyl group having 8 to 10 carbon atoms, a hydroxymethyl group, or

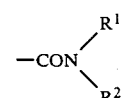

wherein $R^1$ represents a hydrogen atom an alkyl group having 1 to 6 carbon atoms, or an aralkyl group having 7 to 10 carbon atoms and $R^2$ represents an alkyl group having 1 to 6 carbon atoms, or X represents —CH$_2$—Y—R wherein Y represents —O— or —NH— and R represents a straight or branched chain alkyl group having 1 to 6 carbon atoms or an aralkyl group having 7 to 10 carbon atoms, C$^{(+)}$ represents (+) form, His represents as L-histidyl group and C* represents a carbon atom in the L-configuration, m represents an integer of from 1 to 3, and n represents 0 or 1; or a pharmaceutically acceptable salt thereof.

2. An amino acid derivative as claimed in claim 1 represented by formula:

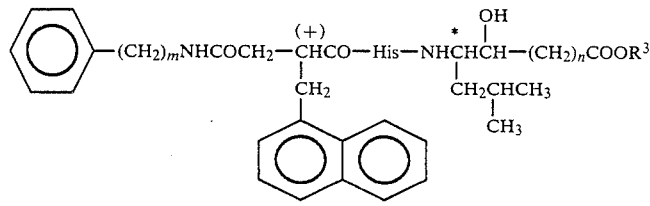

wherein m, C,(+)C*, His and n have the same meanings as defined in claim 1, R³ represents a straight or branched chain alkyl group having 1 to 6 carbon atoms or an aralkyl group having 7 to 9 carbon atoms.

3. An amino acid derivative as claimed in claim 1 represented by formula:

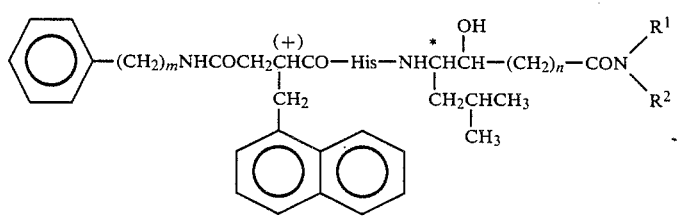

wherein m, C(+), C*, n, His, R¹ and R² have the same meanings as defined in claim 1.

4. An amino acid derivative as claimed in claim 1 represented by formula:

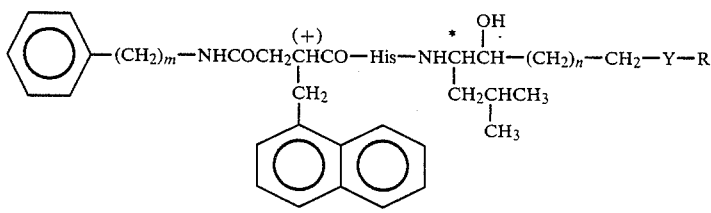

wherein m, C(+), His, C*, n, Y and R have the same meanings as defined in claim 1.

5. An amino acid derivative as claimed in claim 2 represented by formula:

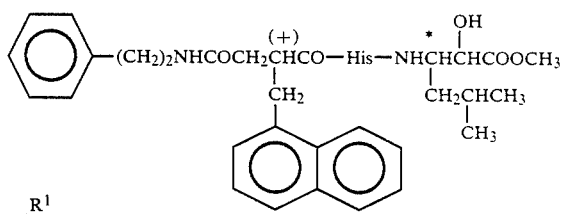

wherein C(+), His and C* have the same meanings as defined in claim 2.

6. An amino acid derivative as claimed in claim 2 represented by formula:

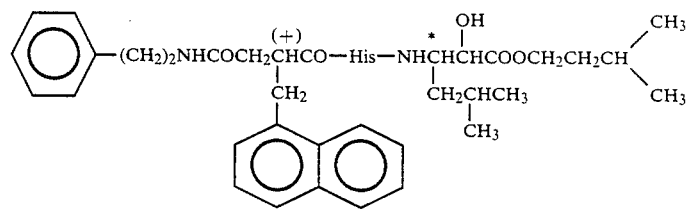

wherein C(+), His and C* have the same meanings as defined in claim 2.

7. An amino acid derivative as claimed in claim 2 represented by formula:

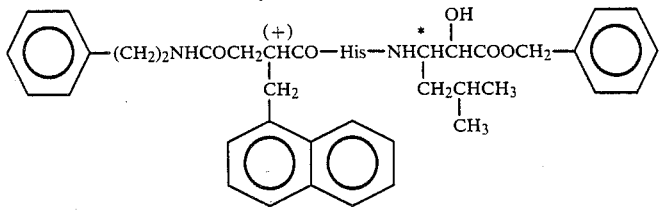

wherein C(+), His and C* have the same meanings as defined in claim 2.

8. An amino acid derivative as claimed in claim 2 represented by formula:

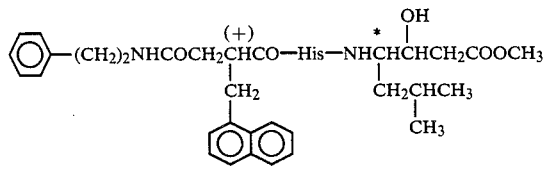

wherein C(+), His and C* have the same meanings as defined in claim 2.

9. An amino acid derivative as claimed in claim 3 represented by formula:

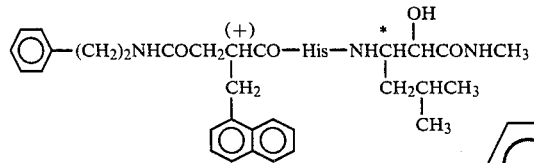

wherein C(+), His and C* have the same meanings as defined in claim 3.

10. An amino acid derivative as claimed in claim 3 represented by formula:

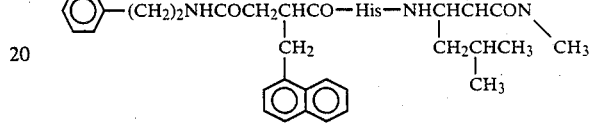

wherein C(+), His and C* have the same meanings as defined in claim 3.

11. An amino acid derivative as claimed in claim 3 represented by formula:

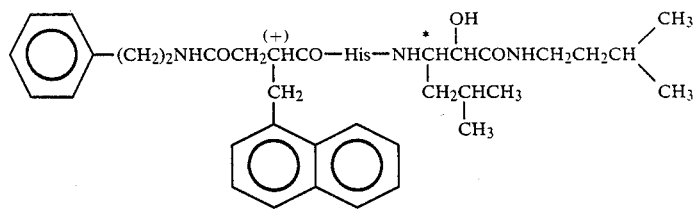

wherein C(+), His and C* have the same meanings as defined in claim 3.

12. An amino acid derivative as claimed in claim 3 represented by formula:

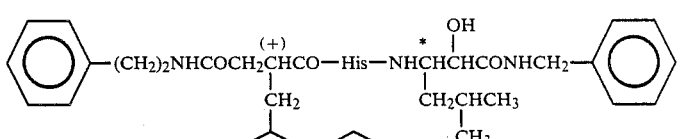

wherein C(+), His and C* have the same meanings as defined in claim 3.

13. An amino acid derivative as claimed in claim 3 represented by formula:

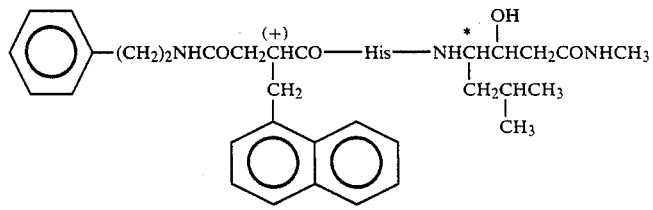

wherein C(+), His and C* have the same meanings as defined in claim 3.

14. An amino acid derivative as claimed in claim 3 represented by formula:

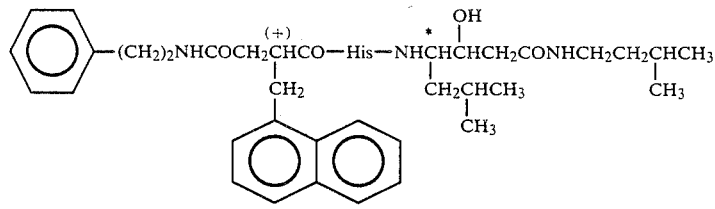

wherein C(+), His and C* have the same meanings as defined in claim 3.

15. An amino acid derivative as claimed in claim 4 represented by formula:

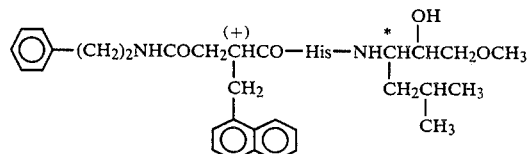

wherein C(+), His and C* have the same meanings as defined in claim 4.

16. An amino acid derivative as claimed in claim 4 represented by formula:

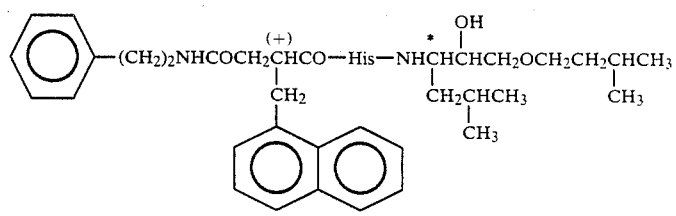

wherein C(+), His and C* have the same meanings as defined in claim 4.

17. An amino acid derivative as claimed in claim 4 represented by formula:

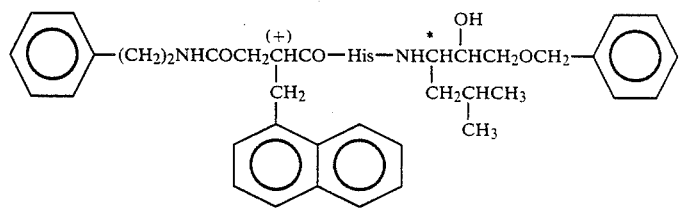

wherein C(+), His and C* have the same meanings as defined in claim 4.

18. An amino acid derivative as claimed in claim 4 represented by formula:

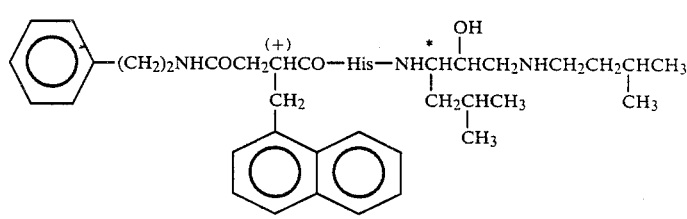

wherein C(+), His and C* have the same meanings as defined in claim 4.

19. An amino acid derivative as claimed in claim 4 represented by formula:

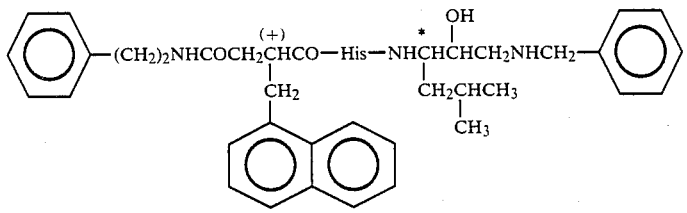
wherein $C^{(+)}$, His and $C^*$ have the same meanings as defined in claim 4.
20. An amino acid derivative as claimed in claim 4 represented by formula:
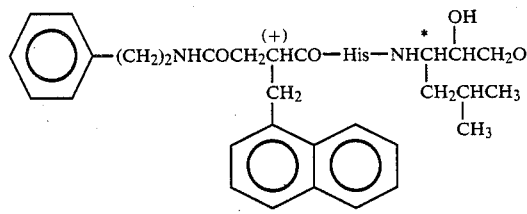
wherein $C^{(+)}$, His and $C^*$ have the same meanings as defined in claim 4.
21. An amino acid derivative as claimed in claim 4 represented by formula:
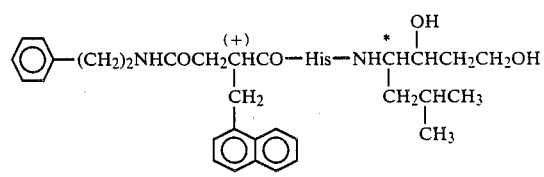
wherein $C^{(+)}$, His and $C^*$ have the same meanings as defined in claim 4.
* * * * *